(12) United States Patent
Dumeunier et al.

(10) Patent No.: US 11,053,188 B2
(45) Date of Patent: Jul. 6, 2021

(54) PROCESS FOR THE PREPARATION OF ENANTIOMERICALLY AND DIASTEREOMERICALLY ENRICHED CYCLOBUTANE AMINES AND AMIDES

(71) Applicant: SYNGENTA PARTICIPATIONS AG, Basel (CH)

(72) Inventors: Raphael Dumeunier, Stein (CH); Tomas Smejkal, Stein (CH); Brijnandan Premnath Mishra, Ilhas Goa (IN); Vijayagopal Raman Gopalsamuthiram, Ilhas Goa (IN); Edouard Godineau, Stein (CH); Anthony Cornelius O'Sullivan, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/764,666

(22) PCT Filed: Nov. 14, 2018

(86) PCT No.: PCT/EP2018/081257
§ 371 (c)(1),
(2) Date: May 15, 2020

(87) PCT Pub. No.: WO2019/096860
PCT Pub. Date: May 23, 2019

(65) Prior Publication Data
US 2020/0407311 A1 Dec. 31, 2020

(30) Foreign Application Priority Data

Nov. 16, 2017 (IN) .............................. 201711041030

(51) Int. Cl.
| | | |
|---|---|---|
| *C07C 231/06* | (2006.01) |
| *C07C 45/44* | (2006.01) |
| *C07C 49/593* | (2006.01) |
| *C07C 49/467* | (2006.01) |
| *C07C 49/647* | (2006.01) |
| *C07C 49/697* | (2006.01) |
| *C07C 49/39* | (2006.01) |
| *C07C 231/02* | (2006.01) |
| *C07C 211/40* | (2006.01) |
| *C07C 45/54* | (2006.01) |
| *C07C 209/26* | (2006.01) |
| *C07D 213/803* | (2006.01) |
| *C07C 47/457* | (2006.01) |
| *C07C 233/58* | (2006.01) |
| *B01J 21/02* | (2006.01) |

(52) U.S. Cl.
CPC .......... *C07C 231/065* (2013.01); *B01J 21/02* (2013.01); *C07C 45/44* (2013.01); *C07C 45/54* (2013.01); *C07C 47/457* (2013.01); *C07C 49/39* (2013.01); *C07C 49/467* (2013.01); *C07C 49/593* (2013.01); *C07C 49/647* (2013.01); *C07C 49/697* (2013.01); *C07C 209/26* (2013.01); *C07C 211/40* (2013.01); *C07C 231/02* (2013.01); *C07C 231/06* (2013.01); *C07D 213/803* (2013.01); *C07B 2200/07* (2013.01); *C07C 233/58* (2013.01); *C07C 2601/02* (2017.05); *C07C 2601/04* (2017.05)

(58) Field of Classification Search
None
See application file for complete search history.

(56) References Cited

U.S. PATENT DOCUMENTS

2016/0157485 A1 6/2016 O'Sullivan et al.

FOREIGN PATENT DOCUMENTS

| WO | 2015003951 A1 | 1/2015 |
| WO | 2015178846 A1 | 11/2015 |

OTHER PUBLICATIONS

Ohshita ("GaCl3-catalyzed skeletal rearrangmement of a,a,a-trisubstituted aldehydes" Org. Lett, 2005, 7(2), p. 331-334) (Year: 2005).*
M.Truong, et al.: "First synthesis of (1S,2S)- and (1R,2R)-1-amino-2-isopropylcyclobutanecarb oxylic acids by asymmertric Strecker reaction from 2-substituted cyclobutanones", Tetrahedron: Asymmetry, vol. 14 (8), pp. 1063-1072, 2003.
M.Yamashita, et al.: "A new synthesis of cyclopentanones by the ring expansion of 1-acyl-1-[p-tolyl(or methyl)thio] cyclobutanes", Tetrahedron Letters, vol. 24 (1), pp. 79-82, Jan. 1983.
M.Yamashita, et al.: "A convenient ring formation of 3-aryl-2,2-dialkyl-2,3-dihydrobenzofurans from phenols and 2-aryl-2,2-dialkylacetaldehydes", Tetrahedron, vol. 60 (12), pp. 2843-2849, 2004.
International Search Report for International Application No. PCT/EP/2018/081257 dated Feb. 12, 2019.

* cited by examiner

*Primary Examiner* — Amy C Bonaparte
(74) *Attorney, Agent, or Firm* — BakerHostetler; Toni-Junell Herbert

(57) ABSTRACT

The present invention relates to a process for the preparation of enantiomerically and diastereomerically enriched cyclobutane amines and amides by reacting (a) cyclopropylcarbonitrile to a cyclopropylcarbaldehyde, (b) further reacting to a cyclobutanone, or (d') further reacting to an enamide, (c) further reacting to enantiomerically and diastereomerically enriched cyclobutane amines, or (d) further reacting to an enamide and (e) to an enantiomerically and diastereomerically enriched cyclobutylamide to obtain (f) an enantiomerically and diastereomerically enriched cyclobutane amine, and (g) further reacting to an enantiomerically and diastereomerically enriched cyclobutane amide.

23 Claims, No Drawings

PROCESS FOR THE PREPARATION OF ENANTIOMERICALLY AND DIASTEREOMERICALLY ENRICHED CYCLOBUTANE AMINES AND AMIDES

CROSS-REFERENCE TO RELATED APPLICATIONS

This application is a 371 National Stage application of International Application No. PCT/EP2018/081257, filed Nov. 14, 2018 which claims priority to IN 201711041030 filed Nov. 16, 2017, the entire contents of which applications are hereby incorporated by reference.

The present invention relates to a process for the preparation of enantiomerically and diastereomerically enriched cyclobutane amines and amides by reacting (a) cyclopropylcarbonitrile to a cyclopropylcarbaldehyde, (b) further reacting to a cyclobutanone, or (d') further reacting to an enamide, (c) further reacting to an enantiomerically and diastereomerically enriched cyclobutane amine, or (d) further reacting to an enamide and (e) to an enantiomerically and diastereomerically enriched cyclobutylamide to obtain (f) an enantiomerically and diastereomerically enriched cyclobutane amine, and (g) further reacting to an enantiomerically and diastereomerically enriched cyclobutane amide.

The present invention relates to a process for the preparation of enantiomerically and diastereomerically enriched cyclobutane amines and amides according to the following Scheme 1.

Preparation methods of compounds of formula (VII) of Scheme 1 have been described in WO2013/143811 and WO2015/003951. The current invention relates to improved methods to prepare compounds of formula (VII), in particular to method steps (a), (b), (c), (d), (d'), (e), (f) and (g).

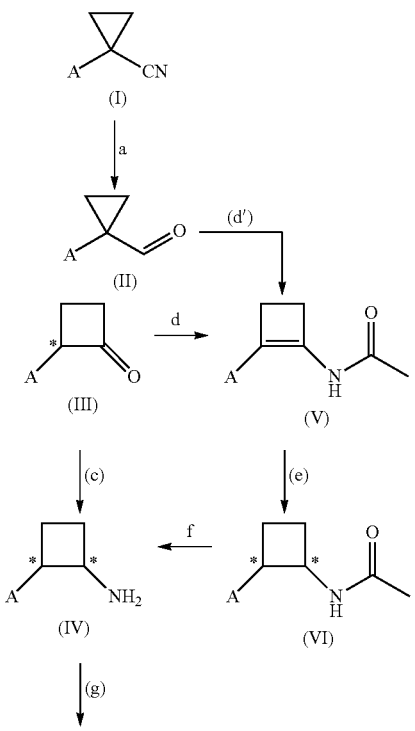

Scheme 1

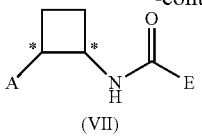

(VII)

wherein A is selected from aryl, heteroaryl, $C_1$-$C_6$-alkyl, $C_2$-$C_6$-alkenyl, $C_2$-$C_6$-alkynyl and $C_3$-$C_7$-cycloalkyl which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl; and wherein E is selected from aryl, heteroaryl, hydrogen, $C_1$-$C_6$-alkyl, $C_2$-$C_6$-alkenyl, $C_2$-$C_6$-alkynyl and $C_3$-$C_7$-cycloalkyl which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl and wherein an asterisk * indicates a stereocentre.

Preferably, A and E in Scheme 1 are selected from aryl and heteroaryl, which aryl and heteroaryl are unsubstituted or substituted with one or more substituents independently selected from halogen, cyano, $C_1$-$C_6$-alkyl, $C_1$-$C_6$-haloalkyl, $C_1$-$C_6$-alkoxy and $C_1$-$C_6$-haloalkoxy. More preferably, A is phenyl and E is heteroaryl, which phenyl and heteroaryl are unsubstituted or substituted with one or more substituents independently selected from halogen, cyano, $C_1$-$C_6$-alkyl, $C_1$-$C_6$-haloalkyl, $C_1$-$C_6$-alkoxy and $C_1$-$C_6$-haloalkoxy. Even more preferably, A is phenyl substituted with one or two halogen and E is a pyridyl substituted with one $C_1$-$C_6$-haloalkyl, in particular A is phenyl substituted with two chloro and E is 3-pyridyl substituted with trifluoromethyl, more particularly A is 2,4-dichlorophenyl and E is (2-trifluoromethyl)-pyrid-3-yl.

In a first aspect of the invention, there is provided a process (a) for the preparation of a compound of formula (II) comprising reducing the nitrile moiety of a compound of formula (I) to an aldehyde wherein the reduction of the nitrile moiety of the compound of formula (I) is carried out via partial hydrogenation to the corresponding intermediate imine applying $H_2$ and a metal catalyst or a metal hydride, followed by subsequent hydrolysis to the compound of formula (II) wherein A is as defined above in Scheme 1. In particular the metal catalyst is selected from Pd/C (palladium on carbon) (a1) and Raney nickel (Ra/Ni) (a2), the metal hydride is selected from DIBAL (diisobutylaluminum hydride) (a3) and REDAL (sodium bis(2-methoxyethoxy) aluminiumhydride) (a4).

Typical reaction parameters for reaction (a) are as follows:

(a1) Transformation of Compound of Formula (I) to a Compound of Formula (II) Using Pd/C:

The transformation of a compound of formula (I) to a compound of formula (II) is typically carried out in the presence of $H_2$, a catalyst such as palladium on a suitable support or a carrier material, optionally a solvent, such as an alcohol or a hydrocarbon, in particular MeOH (methanol), toluene or methylcyclohexane, an organic or an inorganic acid, in particular HCl or trifluoroacetic acid, and water.

Preferred reaction parameters for process (a1) of Scheme 1 are as follows:

Reaction (a1) is preferably carried at a temperature between −10° C. and 150° C., more preferably between 0° C. and 50° C., even more preferably at about 5° C.

The hydrogen gas pressure within the reaction vessel may be between 0.1 and 100 bar, preferably between 0.1 and 20 bar, more preferably between 0.5 and 3 bar.

The reaction mixture is preferably charged with 1-35 mole equivalents of water relative to the compound of formula (I), more preferably between 2-16 mole equivalents and even more preferably between 3-6 mole equivalents.

The reaction mixture is preferably charged with 1-50 mole equivalents of acid relative to the compound of formula (I), more preferably between 2-30 mole equivalents and even more preferably between 4-20 mole equivalents.

Palladium on a suitable support or a carrier material: Particularly, between 0.001 and 1.0 mole equivalents relative to the compound of formula (I) of Pd/C is added. More particularly, between 0.001 and 0.01 mole equivalents relative to the compound of formula (I) of the Pd/C is added.

Preferred conditions are such that the concentration of the compound of formula (I) is 1-30% by weight of the total reaction mixture.

(a2) Transformation of Compound of Formula (I) to a Compound of Formula (II) Using Raney Nickel (Ra/Ni):

The transformation of a compound of formula (I) to a compound of formula (II) is typically achieved in the presence of Hz, a Raney nickel catalyst, an organic acid, in particular acetic acid or trifluoroacetic acid, optionally a catalyst deactivating additive, in particular pyridine or quinoline, and water.

Preferred reaction parameters for process (a2) of Scheme 1 are as follows:

Reaction (a2) is preferably carried out at a temperature between −10° C. and 150° C., more preferably between 0° C. and 50° C., even more preferably at about 25° C.

The hydrogen gas pressure within the reaction vessel may be between 0.1 and 100 bar, preferably between 0.1 and 20 bar, more preferably between 0.5 and 3 bar.

The reaction mixture is preferably charged with 1-60 mole equivalents of water relative to the compound of formula (I), more preferably between 2-40 mole equivalents, and even more preferably between 5-12 mole equivalents The reaction mixture is preferably charged with 1-66 mole equivalents of acid relative to the compound of formula (I).

The reaction mixture is optionally charged with 0.1-25 mole equivalents of a catalyst deactivating additive relative to the compound of formula (I).

Ra/Ni: Particularly, between 0.01 and 1.0 mole equivalents relative to the compound of formula (I) of the Ra/Ni catalyst is added, preferably 0.1-0.5 mole equivalents.

Preferred conditions are such that the concentration of the compound of formula (I) is 1-30% by weight of the reaction mixture.

(a3) Transformation of a Compound of Formula (I) to a Compound of Formula (II) Using DIBAL:

The transformation of a compound of formula (I) to a compound of formula (II) is typically achieved in the presence of DIBAL and an organic solvent, followed by an acidic work-up.

A suitable solvent for reaction (a3) may be selected from the following classes of solvents: ethers or chlorinated and non-chlorinated hydrocarbons or aromatics. Suitable solvents include but are not limited to dichloromethane, tetrahydrofuran, hexanes, heptane, xylenes, toluene and cyclohexane. Preferred solvents are toluene and o-xylene.

Preferred reaction parameters for process (a3) of Scheme 1 are as follows:

Reaction (a3) is preferably carried out at a temperature between −20° C. and 100° C., more preferably between −10° C. and 20° C., even more preferably at about 0° C.

The reaction mixture is preferably charged with 1-2 mole equivalents of DIBAL relative to the compound of formula (I).

Preferred reaction conditions are such that the concentration of the compound of formula (I) is 1-30% by weight of the reaction mixture.

(a4) Transformation of Compound of Formula (I) to a Compound of Formula (II) Using REDAL:

The transformation of a compound of formula (I) to a compound of formula (II) is achieved in the presence of REDAL, an organic solvent, preferably followed by an acidic work-up.

A suitable solvent may be selected from the following classes of solvents: ethers or non-chlorinated hydrocarbons or aromatics. Suitable solvents include but are not limited to THF (tetrahydrofuran), xylenes and toluene. Preferred solvents are toluene and THF.

Preferred reaction parameters for process (a4) of Scheme 1 are as follows:

Reaction (a4) is preferably carried out at a temperature between −20° C. and 100° C., more preferably between −10° C. and 25° C., even more preferably from 0-25° C.

The reaction mixture is preferably charged with 0.5-1.2 mole equivalents of REDAL relative to the compound of formula (I).

Preferred conditions are such that the concentration of the compound of formula (I) is 1-35% by weight of the reaction mixture.

It will be appreciated that any of the preferred features for each of the processes (a1), (a2), (a3) and (a4) may be combined with one or more other preferred features of processes (a1), (a2), (a3) and (a4), respectively.

In a second aspect of the invention, there is provided a process (b) for the preparation of a compound of formula (III) comprising reacting a compound of formula (II) in the presence of a suitable Lewis acid and wherein A is defined as above in Scheme 1. Particularly, the Lewis acid is selected from $AlCl_3$ and $GaCl_3$, preferably $AlCl_3$. Preferably, process (b) is carried out under inert conditions, such as under nitrogen gas, and in a suitable solvent.

A person skilled in the art understands that reaction (b) of Scheme 1 is carried out in a suitable solvent. A suitable solvent may be selected from the following classes of solvents: chlorinated hydrocarbons or chlorinated aromatics. Suitable solvents include but are not limited to dichloromethane, chlorobenzene or dichlorobenzene. Preferred solvents are chlorinated aromatic solvents, in particular dichlorobenzene and chlorobenzene.

Preferred reaction parameters for process (b) of Scheme 1 are as follows:

The reaction (b) is preferably carried out at a temperature between 0° C. and 100° C., more preferably between 20° C. and 80° C., more preferably from 50-60° C.

The reaction mixture is preferably charged with 1.0-1.5 mole equivalents of $AlCl_3$ or $GaCl_3$ relative to the compound of formula (II).

The concentration of the compound of formula (II) is preferably 1-40% by weight of the reaction mixture.

The process conditions for process (b) have been shown to be particularly efficacious, i.e. they lead to higher yields of compounds of formula (III).

It will be appreciated that any of the preferred features for process (b) may be combined with one or more other preferred features for process (b).

In a third aspect of the invention, there is provided a process (c) for the preparation of an enantiomerically and diastereomerically enriched cyclobutane amine comprising reacting a compound of formula (III) with an ammonium salt and $H_2$ in presence of a chiral transition metal catalyst, and wherein A is as defined above in Scheme 1. Optionally, one or more additives are added to the reaction mixture.

The chiral transition metal catalyst comprises a transition metal selected from Ru, Rh, Ir and Pd and a chiral ligand.

Chiral ligands are known in the art and may be used in the present invention, examples are given in "Catalytic asymmetric synthesis", Iwao Ojima, third Edition, Wiley-VCH 2010 and the literature cited therein; typical classes which are known to a person skilled in the art include but are not limited to TADDOL ($\alpha,\alpha,\alpha',\alpha'$-tetraaryl-2,2-disubstituted 1,3-dioxolane-4,5-dimethanol), DUPHOS (phospholane ligand), BOX (bis(oxazoline) ligand), BINAP (2,2'-bis(diphenylphosphino)-1,1'-binaphthyl), BINOL (1,1'-Bi-2-naphthol), DIOP (2,3-O-isopropylidene-2,3-dihydroxy-1,4-bis(diphenylphosphino)butane), WALPHOS, TANIAPHOS, MANDYPHOS, CHENPHOS, JOSIPHOS, BIPHEMP, MeO-BIPHEP, SEGPHOS, CHIRAPHOS, PPHOS, TUNEPHOS and SYNPHOS.

Preferably, the chiral ligand is a bidentate phosphorus containing ligand of the general formula (VIII)

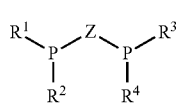

(VIII)

wherein Z is a linking group and $R^1$, $R^2$, $R^3$ and $R^4$ are independently selected from aryl, hetereoaryl, $C_1$-$C_6$-alkyl and $C_1$-$C_6$-cycloalkyl, each of which is unsubstituted or substituted. Typical substituents for $R^1$, $R^2$, $R^3$ and $R^4$ are selected from $C_1$-$C_6$ alkyl, $C_1$-$C_6$ alkoxy, $C_1$-$C_6$ haloalkyl and halogen. Preferably, the linking group Z is selected from (R or S)-1,1'-binaphtyl, (R or S)-4,4'-bi-1,3-benzodioxole, (R or S) 2,2',6,6'-tetramethoxy-3,3'-bipyridine, (R or S)-6,6'-dimethoxy-1,1'-biphenyl, (R or S)-4,4',6,6'-tetramethoxy-1,1'-biphenyl, 2,2'-bis-[(R or S)-α-(dimethylamino)benzyl] ferrocene, ferrocenyl methyl, ferrocene, benzene and ethyl. More preferably, the bidentate ligand of formula (VIII) is selected from BINAP, WALPHOS, JOSIPHOS, TANIAPHOS, MANDYPHOS, CHENPHOS, MeO-BIPHEP, PPHOS, DUPHOS, TUNEPHOS, SYNPHOS and SEPGPHOS classes of ligands. Suitable chiral ligands in the current invention include but are not limited to
(R)-2,2'-bis(diphenylphosphino)-1,1'-binaphtyl,
(S)-2,2'-bis(diphenylphosphino)-1,1'-binaphtyl,
(R)-2,2'-bis(di-p-tolylphosphino)-1,1'-binaphtyl,
(S)-2,2'-bis(di-p-tolylphosphino)-1,1'-binaphtyl,
(R)-2,2'-bis[di(3,5-xylyl)phosphino]-1,1'-binaphtyl,
(S)-2,2'-bis[di(3,5-xylyl)phosphino]-1,1'-binaphtyl,
(R)-5,5'-bis(diphenylphosphino)-4,4'-bi-1,3-benzodioxole,
(S)-5,5'-bis(diphenylphosphino)-4,4'-bi-1,3-benzodioxole,
(R)-5,5'-bis(di[3,5-xylyl]phosphino)-4,4'-bi-1,3-benzodioxole,
(S)-5,5'-bis(di[3,5-xylyl]phosphino)-4,4'-bi-1,3-benzodioxole,
(R)-1,13-bis(diphenylphosphino)-7,8-dihydro-6H-dibenzo[f,h][1,5]dioxin,
(S)-1,13-bis(diphenylphosphino)-7,8-dihydro-6H-dibenzo[f,h][1,5]dioxin,
(R)-2,2',6,6'-tetramethoxy-4,4'-bis(diphenylphosphino)-3,3'-bipyridine,
(S)-2,2',6,6'-tetramethoxy-4,4'-bis(diphenylphosphino)-3,3'-bipyridine,
(R)-2,2',6,6'-tetramethoxy-4,4'-bis(di(3,5-xylyl)phosphino)-3,3'-bipyridine,
(S)-2,2',6,6'-tetramethoxy-4,4'-bis(di(3,5-xylyl)phosphino)-3,3'-bipyridine,
(R)-2,2'-bis(diphenylphosphino)-6,6'-dimethoxy-1,1'-biphenyl,
(S)-2,2'-bis(diphenylphosphino)-6,6'-dimethoxy-1,1'-biphenyl,
(R)-bis(diphenylphosphino)-4,4',6,6'-tetra methoxy-1,1'-biphenyl,
(S)-bis(diphenylphosphino)-4,4',6,6'-tetra methoxy-1,1'-biphenyl,
(R)-6,6'-bis(diphenylphosphino)-2,2',3,3'-tetra hydro-5,5'-bi-1,4-benzodioxin,
(S)-6,6'-bis(diphenylphosphino)-2,2',3,3'-tetra hydro-5,5'-bi-1,4-benzodioxin,
(R)-5,5'-bis(diphenylphosphino)-2,2,2',2'-tetrafluoro-4,4'-bi-1,3-benzodioxole,
(S)-5,5'-bis(diphenylphosphino)-2,2,2',2'-tetrafluoro-4,4'-bi-1,3-benzodioxole,
(R)-(−)-5,5'-bis[di(3,5-di-tert-butyl-4-methoxyphenyl)phosphino]-4,4'-bi-1,3-benzodioxole,
(S)-(+)-5,5'-bis[di(3,5-di-tert-butyl-4-methoxyphenyl)phosphino]-4,4'-bi-1,3-benzodioxole,
(S,S) Fc-1,1'-Bis[bis(3,5-dimethylphenyl)phosphino]-2,2'-bis[(S,S)C—(N,N-dimethylamino)phenylmethyl]ferrocene,
(R,R) Fc-1,1'-Bis[bis(3,5-dimethylphenyl)phosphino]-2,2'-bis[(R,R)C—(N,N-dimethylamino)phenylmethyl]ferrocene,
(R)-2,2'-bis[bis(3,5-diisopropyl-4-dimethylaminophenyl)phosphino]-6,6'-dimethoxy-1,1'-biphenyl,
(S)-2,2'-bis[bis(3,5-diisopropyl-4-dimethylaminophenyl)phosphino]-6,6'-dimethoxy-1,1'-biphenyl,
(S)-2,2'-bis[bis(3,4,5-trimethoxyphenyl)phosphino]-4,4',5,5',6,6'-hexamethoxy-1,1'-biphenyl,
(R)-2,2'-bis[bis(3,4,5-trimethoxyphenyl)phosphino]-4,4',5,5',6,6'-hexamethoxy-1,1'-biphenyl,
(R)-1-diphenylphosphino-2-[(R)-(N,N-dimethylamino)[2-(diphenylphosphino)phenyl]methyl]ferrocene,
(S)-1-diphenylphosphino-2-[(S)-(N,N-dimethylamino)[2-(diphenylphosphino)phenyl]methyl]ferrocene,
(R)-(+)-2,2'-Bis(diphenylphosphino)-5,5',6,6',7,7',8,8'-octahydro-1,1'-binaphthyl,
(S)-(−)-2,2'-Bis(diphenylphosphino)-5,5',6,6',7,7',8,8'-octahydro-1,1'-binaphthyl,
(R)-1-[(R)-1-[bis[3,5-bis(trifluoromethyl)phenyl]phosphino]ethyl]-2-[2-(diphenylphosphino)phenyl]ferrocene,
(S)-1-[(S)-1-[bis[3,5-bis(trifluoromethyl)phenyl]phosphino]ethyl]-2-[2-(diphenylphosphino)phenyl]ferrocene,
(R)-2,2'-bis[bis(3,5-di-tert-butyl-4-methoxyphenyl)phosphino]-6,6'-dimethoxy-1,1'-biphenyl,
(S)-2,2'-bis[bis(3,5-di-tert-butyl-4-methoxyphenyl)phosphino]-6,6'-dimethoxy-1,1'-biphenyl,
(R)-2,2'-bis[di-3,5-xylylphosphino]-6,6'-dimethoxy-1,1'-biphenyl, (S)-2,2'-bis[di-3,5-xylylphosphino]-6,6'-dimethoxy-1,1'-biphenyl,
(R)-1-[(R)-1-(Diphenylphosphino)ethyl]-2-[2-(diphenylphosphino)phenyl]ferrocene,
(S)-1-[(S)-1-(Diphenylphosphino)ethyl]-2-[2-(diphenylphosphino)phenyl]ferrocene,
(R)-2,2'-bis(di-p-dimethylaminophenylphosphino)-6,6'-dimethoxy-1,1'-biphenyl,
(S)-2,2'-bis(di-p-dimethylaminophenylphosphino)-6,6'-dimethoxy-1,1'-biphenyl,
(R)-2,2'-bis[bis(3,5-di-tert-butylphenyl)phosphino]-6,6'-dimethoxy-1,1'-biphenyl,
(S)-2,2'-bis[bis(3,5-di-tert-butylphenyl)phosphino]-6,6'-dimethoxy-1,1'-biphenyl,
(R)-1-[(R)-1-[di(3,5-xylyl)phosphino]ethyl]-2-[2-[di(3,5-xylyl)phosphino]phenyl]ferrocene,
(S)-1-[(R)-1-[di(3,5-xylyl)phosphino]ethyl]-2-[2-[di(3,5-xylyl)phosphino]phenyl]ferrocene,
(R)-2,2'-bis(di-m-dimethylaminophenylphosphino)-6,6'-dimethoxy-1,1'-biphenyl,
(S)-2,2'-bis(di-m-dimethylaminophenylphosphino)-6,6'-dimethoxy-1,1'-biphenyl,
(R)-2,2'-bis[bis(3,5-diisopropyl-4-dimethoxyphenyl)phosphino]-6,6'-dimethoxy-1,1'-biphenyl,
(S)-2,2'-bis[bis(3,5-diisopropyl-4-dimethoxyphenyl)phosphino]-6,6'-dimethoxy-1,1'-biphenyl,
(+1,2-bis[(2S,5S)-2,5-diisopropylphospholano]benzene,
(+)-1,2-bis[(2R,5R)-2,5-diisopropylphospholano]benzene,
(R)-2,2'-bis(di-p-tolylphosphino)-6,6'-dimethoxy-1,1'-biphenyl,
(S)-2,2'-bis(di-p-tolylphosphino)-6,6'-dimethoxy-1,1'-biphenyl,
(R)-2,2'-bis(di-6-methoxy-2-naphthalenylphosphino)-6,6'-dimethoxy-1,1'-biphenyl,
(S)-2,2'-bis(di-6-methoxy-2-naphthalenylphosphino)-6,6'-dimethoxy-1,1'-biphenyl,
(R)-2,2'-bis[bis(3,5-diisopropylphenyl)phosphino]-6,6'-dimethoxy-1,1'-biphenyl,
(S)-2,2'-bis[bis(3,5-diisopropylphenyl)phosphino]-6,6'-dimethoxy-1,1'-biphenyl,
1-Dicyclohexylphosphino-1'-[(S)$_P$—[(S)$_{Fc}$-2-[(R)c-1-(dimethylamino)ethyl]ferrocenyl]phenylphosphino]ferrocene,
1-Dicyclohexylphosphino-1'-[(R)$_P$—[(R)$_{Fc}$-2-[(S)c-1-(dimethylamino)ethyl]ferrocenyl]phenylphosphino]ferrocene.
Preferred chiral ligands are selected from
(R)-2,2'-bis(diphenylphosphino)-1,1'-binaphtyl,
(S)-2,2'-bis(diphenylphosphino)-1,1'-binaphtyl,
(R)-2,2'-bis(di-p-tolylphosphino)-1,1'-binaphtyl,
(S)-2,2'-bis(di-p-tolylphosphino)-1,1'-binaphtyl,
(R)-2,2'-bis[di(3,5-xylyl)phosphino]-1,1'-binaphtyl,
(S)-2,2'-bis[di(3,5-xylyl)phosphino]-1,1'-binaphtyl,
(R)-5,5'-bis(diphenylphosphino)-4,4'-bi-1,3-benzodioxole,
(S)-5,5'-bis(diphenylphosphino)-4,4'-bi-1,3-benzodioxole,
(R)-5,5'-bis(di[3,5-xylyl)phosphino)-4,4'-bi-1,3-benzodioxole,
(S)-5,5'-bis(di[3,5-xylyl)phosphino)-4,4'-bi-1,3-benzodioxole,
(R)-5,5'-bis(di[3,5-di-t-butyl-4-methoxyphenyl]phosphino)-4,4'-bi-1,3-benzodioxole,
(S)-5,5'-bis(di[3,5-di-t-butyl-4-methoxyphenyl]phosphino)-4,4'-bi-1,3-benzodioxole,
(R)-1,13-bis(diphenylphosphino)-7,8-dihydro-6H-dibenzo[f,h][1,5]dioxin,
(S)-1,13-bis(diphenylphosphino)-7,8-dihydro-6H-dibenzo[f,h][1,5]dioxin,
(R)-2,2',6,6'-tetramethoxy-4,4'-bis(diphenylphosphino)-3,3'-bipyridine,
(S)-2,2',6,6'-tetramethoxy-4,4'-bis(diphenylphosphino)-3,3'-bipyridine,
(R)-2,2',6,6'-tetramethoxy-4,4'-bis(di[3,5-xylyl]phosphino)-3,3'-bipyridine,
(S)-2,2',6,6'-tetramethoxy-4,4'-bis(di[3,5-xylyl]phosphino)-3,3'-bipyridine,
(R)-2,2'-bis(diphenylphosphino)-6,6'-dimethoxy-1,1'-biphenyl,
(S)-2,2'-bis(diphenylphosphino)-6,6'-dimethoxy-1,1'-biphenyl,
(R)-bis(diphenylphosphino)-4,4',6,6'-tetramethoxy-1,1'-biphenyl,
(S)-bis(diphenylphosphino)-4,4',6,6'-tetramethoxy-1,1'-biphenyl,
(R)-6,6'-bis(diphenylphosphino)-2,2',3,3'-tetrahydro-5,5'-bi-1,4-benzodioxin,
(S)-6,6'-bis(diphenylphosphino)-2,2',3,3'-tetrahydro-5,5'-bi-1,4-benzodioxin,
(R)-(+)-2,2'-Bis(diphenylphosphino)-5,5',6,6',7,7',8,8'-octahydro-1,1'-binaphthyl,
(S)-(−)-2,2'-Bis(diphenylphosphino)-5,5',6,6',7,7',8,8'-octahydro-1,1'-binaphthyl,
(R)-5,5'-bis(diphenylphosphino)-2,2,2',2'-tetrafluoro-4,4'-bi-1,3-benzodioxole,
(S)-5,5'-bis(diphenylphosphino)-2,2,2',2'-tetrafluoro-4,4'-bi-1,3-benzodioxole,
(R)-1-[(R)-1-[di(3,5-xylyl)phosphino]ethyl]-2-[2-[di(3,5-xylyl)phosphino]phenyl]ferrocene,
(S)-1-[(S)-1-[di(3,5-xylyl)phosphino]ethyl]-2-[2-[di(3,5-xylyl)phosphino]phenyl]ferrocene,
(R)-1-[(R)-1-[bis[3,5-bis(trifluoromethyl)phenyl]phosphino]ethyl]-2-[2-(diphenylphosphino)phenyl]ferrocene and
(S)-1-[(S)-1-[bis[3,5-bis(trifluoromethyl)phenyl]phosphino]ethyl]-2-[2-(diphenylphosphino)phenyl]ferrocene.
More preferably, the chiral ligand is selected from
(R)-2,2'-bis(diphenylphosphino)-1,1'-binaphtyl,
(R)-2,2'-bis(di-p-tolylphosphino)-1,1'-binaphtyl,
(R)-2,2'-bis[di(3,5-xylyl)phosphino]-1,1'-binaphtyl,
(R)-5,5'-bis(diphenylphosphino)-4,4'-bi-1,3-benzodioxole,
(R)-5,5'-bis(di[3,5-xylyl)phosphino)-4,4'-bi-1,3-benzodioxole,
(R)-5,5'-bis(di[3,5-di-tert-butyl-4-methoxyphenyl]phosphino)-4,4'-bi-1,3-benzodioxole,
(S)-1,13-bis(diphenylphosphino)-7,8-dihydro-6H-dibenzo[f,h][1,5]dioxin,
(R)-2,2',6,6'-tetramethoxy-4,4'-bis(di(3,5-xylyl)phosphino)-3,3'-bipyridine,
(R)-2,2'-bis(diphenylphosphino)-6,6'-dimethoxy-1,1'-biphenyl,
(R)-2,2'-bis(diphenylphosphino)-4,4',6,6'-tetramethoxy-1,1'-biphenyl,
(R)-6,6'-bis(diphenylphosphino)-2,2',3,3'-tetrahydro-5,5'-bi-1,4-benzodioxin,
(R)-(+)-2,2'-bis(diphenylphosphino)-5,5',6,6',7,7',8,8'-octahydro-1,1'-binaphthyl,
(R)-(+)-2,2'-bis(di-3,5-xylylphosphino)-5,5',6,6',7,7',8,8'-octahydro-1,1'-binaphthyl,
(R)-5,5'-bis(diphenylphosphino)-2,2,2',2'-tetrafluoro-4,4'-bi-1,3-benzodioxole,
(S)-1-[(S)-1-[di(3,5-xylyl)phosphino]ethyl]-2-[2-[di(3,5-xylyl)phosphino]phenyl]ferrocene,
and
(S)-1-[(S)-1-[bis[3,5-bis(trifluoromethyl)phenyl]phosphino]ethyl]-2-[2-(diphenylphosphino)phenyl]ferrocene.
Even more preferably, the chiral ligand is (R)-2,2'-bis[di(3,5-xylyl)phosphino]-1,1'-binaphtyl.

The transition metal catalyst may consist of a preformed complex. Such preformed complexes may generally be formed by reacting the chiral ligand with a suitable transition metal precursor compound. The complexes thus obtained may then be used as the catalyst in the process (c) of Scheme 1. Transition metal precursor compounds comprise at least the transition metals selected from Ru, Rh, Ir and Pd and typically comprise ligands that are easily displaced by the chiral ligand or it may comprise a ligand that is easily removed by hydrogenation. Preferred transition metal catalysts are Ru complexes.

Suitable transition metal precursor compounds include but are not limited to $RuCl_3$, $RuCl_3 \cdot nH_2O$, $[RuCl_2(\eta_6\text{-benzene})]_2$, $[RuCl_2(\eta_6\text{-cymene})]_2$, $[RuCl_2(\eta_6\text{-mesitylene})]_2$, $[RuCl_2(\eta_6\text{-hexamethylbenzene})]_2$, $[RuBr_2(\eta_6\text{-benzene})]_2$, $[RuI_2(\eta_6\text{-benzene})]_2$, trans-$RuCl_2(DMSO)_4$, $RuCl_2(PPh_3)_3$, $RuCl_2(COD)$ (in which COD=1,5-cyclooctadiene), $Ru(COD)(methylallyl)_2$, $Ru(COD)(trifluoroacetate)_2$, $[Ir(COD)Cl]_2$, $Rh(COD)Cl$, $Rh(COD)_2BF_4$, $Rh(COD)_2(OTf)_2$, $Ru(COD)(OAc)_2$. Preferred transition metal precursor compounds are selected from $[RuCl_2(\eta_6\text{-benzene})]_2$, $[RuCl_2(\eta_6\text{-cymene})]_2$, $RuCl_2(COD)$, $Ru(COD)(methylallyl)_2$ and $Ru(COD)(trifluoroacetate)_2$.

Examples of preformed Ru catalyst complexes include but are not limited to [RuCl(p-cymene)((S)-DM-SEGPHOS)]Cl, [RuCl(p-cymene)((R)-DM-SEGPHOS)]Cl, $[NH_2Me_2][(RuCl((R)\text{-xylbinap}))_2(u\text{-Cl})_3]$, $[NH_2Me_2][(RuCl((S)\text{-xylbinap}))_2(u\text{-Cl})_3]$, $Ru(OAc)_2[(R)\text{-binap}]$, $Ru(OAc)_2[(S)\text{-binap}]$, $Ru(OAc)_2[(R)\text{-xylbinap}]$, $Ru(OAc)_2[(S)\text{-xylbinap}]$, $RuCl_2[(R)\text{-xylbinap}][(R)\text{-daipen}]$, $RuCl_2[(S)\text{-xylbinap}][(S)\text{-daipen}]$, $RuCl_2[(R)\text{-xylbinap}][(R,R)\text{-dpen}]$, $RuCl_2[(S)\text{-xylbinap}][(S,S)\text{-dpen}]$. Preferred Ru catalyst complexes are selected from [RuCl(p-cymene)((R)-xylbinap)]Cl, $[NH_2Me_2][(RuCl((R)\text{-xylbinap}))_2(u\text{-Cl})_3]$, $Ru(OAc)_2[(R)\text{-xylbinap}]$, $[NH_2Me_2][(RuCl((R)\text{—H8-binap}))_2(u\text{-Cl})_3]$, [RuCl(p-cymene)((R)—H8-binap)]Cl, $Ru(OAc)_2[(R)\text{—H8-binap}]$, $[NH_2Me_2][(RuCl((R)\text{—H8-xylbinap}))_2(u\text{-Cl})_3]$, [RuCl(p-cymene)((R)—H8-xylbinap)]Cl, $Ru(OAc)_2[(R)\text{—H8-xylbinap}]$, $[NH_2Me_2][(RuCl((S)\text{-1-}[(S)\text{-1-}[bis[3,5\text{-bis(trifluoromethyl)phenyl}]phosphino]ethyl]\text{-2-}[2\text{-(diphenylphosphino)phenyl}]\text{ferrocene}))_2(u\text{-Cl})_3]$, [RuCl(p-cymene)((S)-1-[(S)-1-[bis[3,5-bis(trifluoromethyl)phenyl]phosphino]ethyl]-2-[2-(diphenylphosphino)phenyl]ferrocene)]Cl and (S)-1-[(S)-1-[bis[3,5-bis(trifluoromethyl)phenyl]phosphino]ethyl]-2-[2-(diphenylphosphino)phenyl]ferrocenel. More preferred Ru catalyst complexes are selected from $[NH_2Me_2][(RuCl((R)\text{-xylbinap}))_2(u\text{-Cl})_3]$ and $Ru(OAc)_2[(R)\text{-xylbinap}]$.

As mentioned above, process (c) in Scheme 1 also requires the presence of an ammonium salt. Ammonium salts may be generated in situ by adding ammonia and the appropriate acid. In particular, the acids are selected from compounds of formula

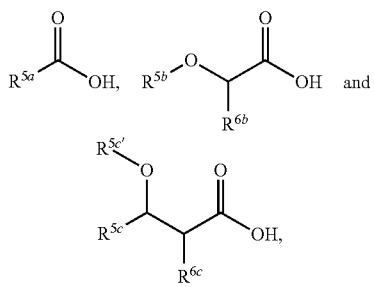

wherein $R^{5a}$ is selected from $C_1$-$C_6$-alkyl, —($C_0$-$C_3$-alkyl)-$C_3$-$C_6$-cycloalkyl, —($C_0$-$C_3$-alkyl)-$C_3$-$C_6$-heterocycloalkyl, —($C_0$-$C_3$-alkyl)-$NR^{5a1}R^{5a2}$, —($C_0$-$C_3$-alkyl)-aryl and —($C_0$-$C_3$-alkyl)-heteroaryl which $C_1$-$C_6$-alkyl, —($C_0$-$C_3$-alkyl)-$C_3$-$C_6$-cycloalkyl, —($C_0$-$C_3$-alkyl)-$C_3$-$C_6$-heterocycloalkyl, —($C_0$-$C_3$-alkyl)-aryl and —($C_0$-$C_3$-alkyl)-heteroaryl are unsubstituted or substituted with one or more substituents independently selected from halogen, OH, $C_1$-$C_6$-alkyl, $C_1$-$C_6$-haloalkyl, $C_1$-$C_6$-alkoxy and $C_1$-$C_6$-haloalkoxy; $R^{5a1}$ and $R^{5a2}$ are independently selected from hydrogen and $C_1$-$C_6$-alkyl;

$R^{5b}$ and $R^{5b'}$ are selected from hydrogen, $C_1$-$C_6$-alkyl, —($C_0$-$C_3$-alkyl)-$C_3$-$C_6$-cycloalkyl, —($C_0$-$C_3$-alkyl)C(=O)OH, —($C_0$-$C_3$-alkyl)-aryl and —($C_0$-$C_3$-alkyl)-heteroaryl which $C_1$-$C_6$-alkyl, —($C_0$-$C_3$-alkyl)-$C_3$-$C_6$-cycloalkyl, —($C_0$-$C_3$-alkyl)-aryl and —($C_0$-$C_3$-alkyl)-heteroaryl are unsubstituted or substituted with one or more substituents independently selected from halogen, $C_1$-$C_6$-alkyl, $C_1$-$C_6$-haloalkyl, $C_1$-$C_6$-alkoxy and $C_1$-$C_6$-haloalkoxy;

$R^{5b}$, $R^{6b}$ and $R^{6c}$ are selected from hydrogen, halogen, $C_1$-$C_6$-alkyl, —($C_0$-$C_3$-alkyl)-$C_3$-$C_6$-cycloalkyl, —($C_0$-$C_3$-alkyl)-aryl and —($C_0$-$C_3$-alkyl)heteroaryl which $C_1$-$C_6$-alkyl, —($C_0$-$C_3$-alkyl)-$C_3$-$C_6$-cycloalkyl, —($C_0$-$C_3$-alkyl)-aryl and —($C_0$-$C_3$-alkyl)-heteroaryl are unsubstituted or substituted with one or two substituents independently selected from halogen, $C_1$-$C_6$-alkyl, $C_1$-$C_6$-haloalkyl, $C_1$-$C_6$-alkoxy and $C_1$-$C_6$-haloalkoxy.

In particular, the acids are selected from compounds of formula

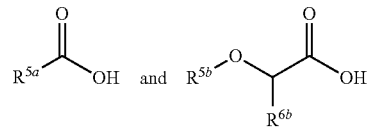

$R^{5a}$ is selected from $C_1$-$C_6$-alkyl, —($C_0$-$C_3$-alkyl)-$C_3$-$C_6$-cycloalkyl, —($C_0$-$C_3$-alkyl)-$C_3$-$C_6$-heterocycloalkyl, —($C_0$-$C_3$-alkyl)-aryl and —($C_0$-$C_3$-alkyl)-heteroaryl which $C_1$-$C_6$-alkyl, —($C_0$-$C_3$-alkyl)-$C_3$-$C_6$-cycloalkyl, —($C_0$-$C_3$-alkyl)-$C_3$-$C_6$-heterocycloalkyl, —($C_0$-$C_3$-alkyl)-aryl and —($C_0$-$C_3$-alkyl)-heteroaryl are unsubstituted or substituted with one or more substituents independently selected from halogen, OH, $C_1$-$C_6$-alkyl, $C_1$-$C_6$-haloalkyl, $C_1$-$C_6$-alkoxy and $C_1$-$C_6$-haloalkoxy; $R^{5b}$ is selected from $C_1$-$C_6$-alkyl, —($C_0$-$C_3$-alkyl)-$C_3$-$C_6$-cycloalkyl, —($C_0$-$C_3$-alkyl)-aryl and —($C_0$-$C_3$-alkyl)-heteroaryl which $C_1$-$C_6$-alkyl, —($C_0$-$C_3$-alkyl)-$C_3$-$C_6$-cycloalkyl, —($C_0$-$C_3$-alkyl)-aryl and —($C_0$-$C_3$-alkyl)-heteroaryl are unsubstituted or substituted with one or more substituents independently selected from halogen, $C_1$-$C_6$-alkyl, $C_1$-$C_6$-haloalkyl, $C_1$-$C_6$-alkoxy and $C_1$-$C_6$-haloalkoxy; $R^{6b}$ is selected from hydrogen, halogen, $C_1$-$C_6$-alkyl, $C_3$-$C_6$-cycloalkyl, aryl and heteroaryl which $C_1$-$C_6$-alkyl, $C_3$-$C_6$-cycloalkyl, aryl and heteroaryl are unsubstituted or substituted with one or two substituents independently selected from halogen, $C_1$-$C_6$-alkyl, $C_1$-$C_6$-haloalkyl, $C_1$-$C_6$-alkoxy and $C_1$-$C_6$-haloalkoxy.

More particularly, acids are selected from acetic acid, methoxyacetic acid, 2-methoxypropionic acid, tetrahydrofuran-2-carboxylic acid, o-methoxybenzoic acid, p-methoxybenzoic acid, phenoxy acetic acid, 2-furan-carboxylic acid, p-chlorophenoxy acetic acid, salicylic acid, 4-tert-butylphenoxyacetic acid, acetic acid and chloroacetic acid, even more particularly phenoxy acetic acid.

Ammonium salts may also be added preformed into the reaction mixture. In particular, ammonium salts are selected from ammonium acetate, ammonium 2-methoxypropionate, ammonium tetrahydrofuran-2-carboxylate, ammonium o-methoxybenzoate, ammonium p-methoxybenzoate, ammonium chloroacetate, ammonium methoxyacetate, ammonium phenoxyacetate, ammonium p-chlorophenoxy acetate, ammonium 4-tert-butylphenoxy acetate, ammonium furan-2-carboxylate and ammonium salicylate, more particularly ammonium phenoxy acetate.

A person skilled in the art understands that process (c) of Scheme 1 is carried out in a suitable solvent. A suitable solvent may be selected from the following classes of solvents: alcohols, ethers, esters, chlorinated or non-chlorinated hydrocarbons and aromatics. Suitable solvents include but are not limited to methanol, ethanol, 2,2,2-trifluoroethan-1-ol, dichloromethane and toluene. Preferred solvents are alcohols, in particular methanol.

Process (c) of Scheme 1 is carried out in the presence of hydrogen gas ($H_2$). The hydrogen gas pressure within the reaction vessel may be between 1 and 500 bar, in particular between 1 and 250 bar, more particularly between 1 and 50 bar, even more particularly between 5 and 30 bar.

Typically, the temperature of reaction (c) of Scheme 1 is between 0 and 150° C., preferably between 30 and 120° C., more preferably between 50 and 100° C., even more preferably between 70 and 90° C.

Additives may also be added to process (c) of Scheme 1. Suitable additives may be selected from ammonium salts, ammonia, acids, drying agents like molecular sieves and magnesium sulfate, iodine and alcohols. Examples of additives which may be added include but are not limited to chloroacetic acid, trifluoroacetic acid, methoxyacetic acid, salicylic acid, phenoxy acetic acid, furan-2-carboxylic acid, 2-methoxybenzoic acid, N-methylglycine, acetic acid, ammonium bromide, ammonium chloride, iodine, 2,2,2-trifluoroethanol, magnesium sulfate, molecular sieve materials. Preferred additives are ammonium salts or acids, e.g. ammonium halogens such as $NH_4Cl$ or or carboxylic acids such as phenoxy acetic acid.

The skilled person understands that the pH of the reaction mixture may influence the outcome of the reaction. Typically, the pH of the reaction mixture is between 2 and 7, preferably between 4 and 7 and even more preferably between 6 and 7.

Preferred process parameters for reaction (c) of Scheme 1 are as follows:

The transition metal catalyst is added to the reaction mixture in an amount of 0.0001 and 0.1 mole equivalents relative to the compound of formula (III). Particularly, between 0.0005 and 0.01 mole equivalents relative to the compound of formula (III) is added.

Transition metal catalysts may be pre-formed or may be formed in situ by adding the chiral ligands and the transition metal precursors into the reaction mixture. A skilled person is well aware of the formation of transition metal catalysts in situ, e.g. as disclosed in EP1153908A2.

The reaction mixture is charged preferably (i) with 1-10 mole equivalents relative to the compound of formula (III) of a pre-formed ammonium salt or (ii) charged with 1-10 mole equivalents relative to the compound of formula (III) of ammonia and the corresponding acid to form the ammonium salt in situ.

The concentration of the compound of formula (III) is preferably 1-30% by weight of the reaction mixture.

Optionally, 0.01-2 mole equivalents relative to the compound of formula (III) of one or more additives are added to the reaction mixture.

Preferably, process (c) provides the cis-stereoisomers of compounds of formula (IV) in an e.e. of 50% or higher, preferably of 75% or higher, more preferably 80% or higher. More preferably, process (c) provides the cis-stereoisomers of compounds of formula (IV) in an e.e. (S,S) of 50% or higher, preferably of 75% or higher, more preferably 80% or higher.

It will be appreciated that any of the preferred features for process (c) may be combined with one or more other preferred features of process (c).

In a fourth aspect of the invention, there is provided a process (d) for the preparation of a compound of formula (V) which comprises reacting a compound of formula (III) with acetonitrile in presence of a Lewis acid or a Broensted acid and a suitable additive, and wherein A is as defined above for Scheme 1.

Process (d) of Scheme 1 are carried out either in acetonitrile or a suitable solvent. A suitable solvent may be selected from the following classes of solvents: chlorinated hydrocarbons or aromatics. Suitable solvents include but are not limited to dichloromethane, chlorobenzene or dichlorobenzene. Preferred solvents are chlorinated aromatics, in particular 1,2-dichlorobenzene.

Suitable Lewis acids or Broensted acids include but are not limited to $AlCl_3$, $GaCl_3$, $FeCl_3$, $BF_3.Et_2O$, $HBF_3.Et_2O$, triflic acid, nonaflic acid (perfluorobutanesulfonic acid), $MeSO_3H$ and Eaton's reagent (7.7 wt % phosphorous pentoxide in methanesulfonic acid).

Suitable additives may be acyl chlorides, anhydrides or esters. Examples of additives which may be added include but are not limited to acetyl chloride, isopropenyl acetate, 4-methoxybenzoyl chloride and p-anisic anhydride.

Preferred reaction parameters for process (d) of Scheme 1 are as follows:

A temperature between 0° C. and 100° C. for reaction (d) is preferred, more preferably between 20° C. and 80° C., even more preferably at about 50° C.

The reaction mixture is preferably charged with 1.0-2.5 mole equivalents relative to the compound of formula (III) of a Lewis acid or Broensted acid.

The reaction mixture is preferably charged with 1-10 mole equivalents relative to the compound of formula (III) of acetonitrile.

The reaction mixture is preferably charged with 0.25-2.0 mole equivalents relative to the compound of formula (III) of an additive.

The concentration of the compound of formula (III) is preferably 1-30% by weight of the reaction mixture.

It will be appreciated that any of the preferred features for process (d) may be combined with one or more other preferred features of process (d).

In a fifth aspect of the invention, the compound of formula (V) can be prepared via process (d') which is a combination of process (b) and (d) with the difference that compound (III) is not isolated but directly transformed into compound (V). The transformation of a compound (II) to a compound (III) is achieved in the presence of a Lewis acid as described in the second aspect of the invention. The subsequent transformation of a compound (III) to a compound (V) is achieved by adding acetonitrile and an additive as described in the fourth aspect of the invention. Preferably, process (d') is carried out under inert conditions, such as under nitrogen gas, and in a suitable solvent.

A person skilled in the art understands that processes (d) and (d') of Scheme 1 are carried out in a suitable solvent. A suitable solvent may be selected from the following classes of solvents: chlorinated hydrocarbons or aromatics. Suitable solvents include but are not limited to dichloroethane, chlorobenzene or dichlorobenzene. Preferred solvents are chlorinated aromatic, in particular 1,2-dichlorobenzene.

Suitable catalyst/Lewis acid include but are not limited to $AlCl_3$ and $GaCl_3$, preferably $AlCl_3$.

Suitable additives may be acyl chlorides, anhydrides or esters. Examples of additives which may be added include but are not limited to acetyl chloride, isopropenyl acetate, 4-methoxybenzoyl chloride or p-anisic anhydride.

Preferred reaction parameters for process (d') of Scheme 1 correspond to the preferred reaction conditions already described for the transformation of a compound (II) to a compound (III) (step b) and the transformation of a compound (III) to a compound (V) (step d) (second & fourth aspect of the inventions).

It will be appreciated that any of the preferred features for process (d') may be combined with one or more other preferred features of processes (d') and (d).

In a sixth aspect of the invention, there is provided a process (e) for the preparation of a compound of formula (VI) which comprises reacting a compound of formula (V) with $H_2$ in the presence of a chiral or enantioenriched catalyst in analogy to what has been disclosed in WO 2015/003951.

The chiral transition metal catalyst comprises a transition metal selected from Ru and Rh and a chiral ligand.

Chiral ligands are known in the art and may be used in the present invention, examples are given in "Catalytic asymmetric synthesis", Iwao Ojima, third Edition, Wiley-VCH 2010 and the literature cited therein; typical classes which are known to a person skilled in the art include but are not limited to TADDOL ($\alpha,\alpha,\alpha',\alpha'$-tetraaryl-2,2-disubstituted 1,3-dioxolane-4,5-dimethanol), DUPHOS (phospholane ligand), BOX (bis(oxazoline) ligand), BINAP (2,2'-bis(diphenylphosphino)-1,1'-binaphthyl), BINOL (1,1'-Bi-2-naphthol), DIOP (2,3-O-isopropylidene-2,3-dihydroxy-1,4-bis(diphenylphosphino)butane), WALPHOS, TANIAPHOS, MANDYPHOS, CHENPHOS, JOSIPHOS, BIPHEMP, MeO-BIPHEP, SEGPHOS, CHIRAPHOS, PPHOS, QUINOX-P, NORPHOS, TUNEPHOS and SYNPHOS.

Preferably, the chiral ligand is a bidentate phosphor containing ligand of the general formula (IX)

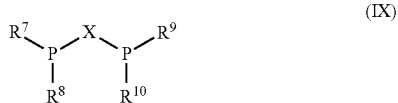

(IX)

wherein X is a linking group and $R^7$, $R^8$, $R^9$ and $R^{10}$ are independently selected from aryl, hetereoaryl, $C_1$-$C_6$-alkyl and $C_1$-$C_6$-cycloalkyl, each of which is unsubstituted or substituted. Preferably, the linking group X is selected from (R or S) 1,1'-binaphtyl, (R or S)-4,4'-bi-1,3-benzodioxole, (R or S)-2,2',6,6'-tetramethoxy-3,3'-bipyridine, (R or S)-6,6'-dimethoxy-1,1'-biphenyl, (R or S)-4,4',6,6' tetramethoxy-1,1'-biphenyl, 2,2'-bis-[(R or S)-cx-(dimethylamino)benzyl] ferrocene, ferrocenyl methyl, ferrocene, benzene and ethyl. More preferably, the bidentate ligand of formula (IX) is selected from BINAP, MANDYPHOS, JOSIPHOS, MeO-BIPHEP, TANIAPHOS, CHENPHOS, QUINOX-P and DUPHOS classes of ligands.

Suitable chiral ligands in the current invention include but are not limited to (R)-1-[(S)-2-(Di-tert-butylphosphino)ferrocenyl]ethyldi-o-tolylphosphine, (R,R)$_{Fc}$-1,1'-Bis[bis(4-methoxy-3,5-dimethylphenyl)phosphino]-2,2'-bis[(S,S)c-(N,N-dimethylamino)phenylmethyl]ferrocene, (R)-1-[(S)-2-cyclohexylphosphino)ferrocenyl]ethyl bis(2-methylphenyl)-phosphine, (S)-1-Diphenylphosphino-2-[(S)-(N,N-dimethylamino)[2-(diphenylphosphino)phenyl]methyl]ferrocene, (R,R)-(−)-2,3-Bis(tert-butylmethylphosphino)quinoxaline, (2S,3S)-(+2,3-Bis(diphenylphosphino)bicyclo[2.2.1]hept-5-ene, (S)-2,2'-Bis(diisopropylphosphino)-6,6'-dimethoxy-1,1'-biphenyl, (2S,4S)-(−)-2,4-Bis(diphenylphosphino)pentane, 1,1'-Bis[(R)$_P$—[(R)$_{Fc}$-2-[(S)c-1-(dimethylamino)ethyl]ferrocenyl]phenylphosphino]ferrocene, 1-Dicyclohexylphosphino-1'-[(S)$_P$—[(S)$_{Fc}$-2-[(R)C-1-(dimethylamino)ethyl]ferrocenyl]phenylphosphino]ferrocene, (R)-1-[(S)-2-(Diphenylphosphino)ferrocenyl]ethyldi(3,5-xylyl)phosphine, (R)Fc-1-[(S)P-tert-Butylphosphinoyl]-2-[(S)-1-(diphenylphosphino)ethyl]ferrocene, (S)-1-[(R)-2-(Diphenylphosphino)ferrocenyl]ethyldi-tert-butylphosphine, (S)-1-[(R)-2-(Diphenylphosphino)ferrocenyl]ethyldicyclohexylphosphine ethanol adduct, (R)-2,2'-Bis(diphenylphosphino)-6,6'-dimethoxy-1,1'-biphenyl, (R)-(+)-1,2-Bis(diphenylphosphino)propane, (R)-1-[(S)-2-[Di(1-naphthyl)phosphino]ferrocenyl]ethyldi-tert-butylphosphine, (S)-1-[(R)-2-[Di(2-furyl)phosphino]ferrocenyl]ethyldi-tert-butylphosphine, (R)-1-[(S)-2-(Di-tert-butylphosphino)ferrocenyl]ethyldiphenylphosphine, (S)-1-[(R)-2-(Diphenylphosphino)ferrocenyl]ethyldi-tert-butylphosphine, (R)-1-[(S)-2-(Dicyclohexylphosphino)ferrocenyl]ethyldicyclohexylphosphine, (S)-1-[(R)-2-[Bis(4-methoxy-3,5-dimethylphenyl)phosphino]ferrocenyl]ethyldicyclohexylphosphine, (S)-1-[(R)-2-[Bis(4-methoxy-3,5-dimethylphenyl)phosphino]ferrocenyl]ethyldi-tert-butyl-phosphine, (S)-(+)-2,2'-Bis[di(3,5-xylyl) phosphino]-1,1'-binaphthyl, (S)-2,2'-Bis[di-3,5-xylylphosphino]-6,6'-dimethoxy-1,1'-biphenyl, (−)-1,2-Bis((2S,5S)-2,5-diethylphospholano)benzene, (S,S)Fc-1,1'-Bis[bis(4-methoxy-3,5-dimethylphenyl)phosphino]-2,2'-bis[(R,R)C—(N,N-dimethylamino)phenylmethyl]ferrocene, (R)-1-Diphenylphosphino-2-[(R)-(N,N-dimethylamino)[2-(diphenylphosphino)phenyl]methyl]ferrocene, (R)-2,2'-Bis[bis(3,5-di-tert-butyl-4-methoxyphenyl)phosphino]-6,6'-dimethoxy-1,1'-biphenyl, (S)-1-[(R)-2-(Diphenylphosphino)ferrocenyl]ethyldi(3,5-xylyl)phosphine, (S,S)-(−)-2,3-Bis(tert-butylmethylphosphino)quinoxaline, (2S,3S)-(+)-2,3-Bis(diphenylphosphino)butane, (S)-2,2'-Bis(diphenylphosphino)-6,6'-dimethoxy-1,1'-biphenyl, (S)-(+)-1,2-Bis(diphenylphosphino)propane, (S,S)-(+)-1,2-Bis(t-butylMethylphosphino)benzene, (−)-1,2-Bis[(2S,5S)-2,5-dimethylphospholano]benzene, (+)-1,2-Bis[(2S,5S)-2,5-diethylphospholano]benzene,
(−)-1,2-Bis((2R,5R)-2,5-diethylphospholano)ethane.

Preferred chiral ligands in combination with Rh are selected from
(R)-1-[(S)-2-(Di-tert-butylphosphino)ferrocenyl]ethyldi-o-tolylphosphine,
(R)-1-[(S)-2-cyclohexylphosphino)ferrocenyl]ethyl bis(2-methylphenyl)-phosphine and
(R)-1-[(S)-2-(Di-tert-butylphosphino)ferrocenyl]ethyldiphenylphosphine.

Preferred chiral ligands in combination with Ru are selected from
(S)-(+)-2,2'-Bis[di(3,5-xylyl) phosphino]-1,1'-binaphthyl,
(−)-1,2-Bis((2S,5S)-2,5-diethylphospholano)benzene,
(S,S)-(−)-2,3-Bis(tert-butylmethylphosphino)quinoxaline,
(S,S)-(+)-1,2-Bis(t-butylmethylphosphino)benzene,
(−)-1,2-Bis[(2S,5S)-2,5-dimethylphospholano]benzene,
(+)-1,2-Bis[(2S,5S)-2,5-diethylphospholano]benzene,
(S)-1-[(R)-2-[Bis(4-methoxy-3,5-dimethylphenyl)phosphino]ferrocenyl]ethyldi-tert-butyl-phosphine, and
(S)-1-[(R)-2-[Bis(4-methoxy-3,5-dimethylphenyl)phosphino]ferrocenyl]ethyldicyclohexylphosphine.

The transition metal catalyst may consist of a preformed complex. Such preformed complexes may generally be formed by reacting the chiral ligand with a suitable transition metal precursor compound. The complexes thus obtained may then be used as the catalyst in the process (e) of Scheme 1. Transition metal precursor compounds comprise at least the transition metals Ru and Rh and typically comprises ligands that are easily displaced by the chiral ligand or it may comprise a ligand that is easily removed by hydrogenation.

Suitable transition metal precursor compounds include but are not limited to [Rh(COD)$_2$]O$_3$SCF$_3$, [Rh(COD)$_2$]BF$_4$, [Rh(COD)$_2$]BARF (in which BARF=tetrakis[3,5-bis(trifluoromethyl)phenyl]borate), [Rh(nbd)$_2$]BF$_4$ (in which nbd=norbornadiene), bis(2-methallyl)(COD)ruthenium, bis(COD)tetra[u-trifluoroacetato]diruthenium(II) hydrate and [Ru(COD)(2-metallyl)$_2$].

Examples of preformed Rh catalyst complexes include but are not limited to
[Rh(COD)((R)-1-[(S)-2-(Di-tert-butylphosphino)ferrocenyl]ethyldi-o-tolylphosphine)]BF$_4$,
[Rh(COD)((R)-1-[(S)-2-cyclohexylphosphino)ferrocenyl]ethyl bis(2-methylphenyl)-phosphine]BF$_4$,
[Rh(COD)((R)-1-[(S)-2-(Di-tert-butylphosphino)ferrocenyl]ethyldiphenylphosphine)]BF$_4$,
[Rh(COD)((R)-1-[(S)-2-(Di-tert-butylphosphino)ferrocenyl]ethyldi-o-tolylphosphine)]O$_3$SCF$_3$,
[Rh(COD)((R)-1-[(S)-2-cyclohexylphosphino)ferrocenyl]ethyl bis(2-methylphenyl)-phosphine]O$_3$SCF$_3$,
and
[Rh(COD)((R)-1-[(S)-2-(Di-tert-butylphosphino)ferrocenyl]ethyldiphenylphosphine)]O$_3$SCF$_3$.

Preferred reaction parameters for process (e) of Scheme 1:

A person skilled in the art understands that process (e) of Scheme 1 is carried out in a suitable solvent. A suitable solvent may be selected from the following classes of solvents: alcohols, ethers, esters, chlorinated or non-chlorinated hydrocarbons or aromatics. Preferred solvents when a Rh catalyst is used are selected from methanol, isopropanol and 2,2,2-trifluoroethan-1-ol. Preferred solvents are alcohols, in particular trifluoroethanol and isopropanol. Preferred solvents when a Ru catalyst is used are selected from alcohols, in particular isopropanol.

Process (e) of Scheme 1 is carried out in the presence of hydrogen gas (H$_2$). The hydrogen gas pressure within the reaction vessel may be between 1 and 500 bar, in particular between 1 and 250 bar, more particularly between 1 and 50 bar, even more particularly between 10 and 50 bar.

Typically, the temperature of process (e) of Scheme 1 is between 0 and 150° C., preferably between 30 and 120° C., more preferably between 20 and 100° C., even more preferably between 25 and 60° C.

The catalyst amount is between 0.0001 and 0.1 mole equivalents relative to the compound of formula (V) of the transition metal catalyst is added. Particularly, between 0.0001 and 0.005 mole equivalents relative to the compound of formula (V) of the transition metal catalyst is added. Transition metal catalysts may be preformed or may be formed in situ by adding the chiral ligands and the transition metal precursors into the reaction mixture.

The concentration of the compound of formula (V) is preferably 1-30% by weight of the reaction mixture.

This process (e) provides enantiomerically and diastereomerically enriched amides of formula (VI) an e.e. (enantiomeric excess) of 75% or higher, preferably 80% or higher. Preferably, process (e) provides the cis-enantiomers of compounds of formula (IV) in an e.e. of 75% or higher, more preferably 80% or higher.

It will be appreciated that any of the preferred features for process (e) may be combined with one or more other preferred features of process (e).

In a seventh aspect of the invention, there is provided a process (f) for the preparation of a compound of formula (IV) which comprises reacting a compound of formula (VI) under acidic or basic conditions, preferably under acidic conditions.

Suitable acids include but are not limited to HCl, H$_2$SO$_4$, H$_3$PO$_4$, methanesulfonic acid, p-toluenesulfonic acid and trifluoromethanesulfonic acid.

A person skilled in the art understands that process (f) of Scheme 1 is carried out in a suitable solvent. A suitable solvent may be selected from the following classes of solvents: water, alcohols, ethers, esters, chlorinated or non-chlorinated hydrocarbons or aromatics. Suitable solvents include but are not limited to water and toluene. Preferred solvent is water.

Typical reaction parameters for process (f) of Scheme 1 are as follows:

The preferred conditions for the deacetylation are a temperature between 0° C. and 200° C., more specifically between 100° C. and 180° C., in particular at reflux conditions for the corresponding system.

Acid: The application of 1.0-7.0 mole equivalents relative to the compound of formula (VI) proved to be favorable.

Reaction Volume: Typical conditions are such that the concentration of the compound of formula (VI) is 1-30% by weight of the reaction mixture.

It will be appreciated that any of the preferred features for process (f) may be combined with one or more other preferred features of process (f).

In an eighth aspect of the invention, there is provided a process (g) for the preparation of a compound of formula (VII) comprising reacting a compound of formula (IV) with a compound of formula (X)

(X)

wherein Y is a suitable leaving group such as OH, OR or halogen, preferably chloro, R is $C_1$-$C_6$-alkyl, and A and E is as defined previously for Scheme 1.

The reaction of a compound of formula (IV) with a compound of formula (X) is carried out under typical amide bond formation conditions which are known to a person skilled in the art. For example, the reaction (g) includes the addition of a suitable base. Suitable bases include but are not limited to $Et_3N$, $NaHCO_3$ and NaOH.

A person skilled in the art understands that reaction (g) of Scheme 1 is carried out in a suitable solvent. A suitable solvent may be selected from the following classes of solvents: ethers, esters, chlorinated or non-chlorinated hydrocarbons or aromatics. Suitable solvents include but are not limited to toluene, xylene, THF, MeTHF (methyl tetrahydrofuran) and acetonitrile.

Preferred reaction parameters for process (g) of Scheme 1 are as follows:

Reaction (g) is preferably carried out at a temperature between 0° C. and 200° C., more preferably between 100° C. and 180° C., even more preferably between 40 to 60° C.

1.0-3.0 mole equivalents relative to the compound of formula (IV) of base is preferably added.

0-20 mole equivalents relative to the compound of formula (IV) of water is preferably added to the reaction mixture.

The concentration of the compound of formula (IV) is preferably 1-30% by weight of the reaction mixture.

It will be appreciated that any of the preferred features for process (g) may be combined with one or more other preferred features for process (g).

Definitions

The term "alkyl" as used herein—in isolation or as part of a chemical group—represents straight-chain or branched hydrocarbons, preferably with 1 bis 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Alkyl groups with 1 to 4 carbon atoms are preferred, for example methyl, ethyl, n-propyl, isopropyl, n-butyl, isobutyl, s-butyl or t-butyl.

The term "alkenyl"—in isolation or as part of a chemical group—represents straight-chain or branched hydrocarbons, preferably with 2 bis 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Alkenyl groups with 2 to 4 carbon atoms are preferred, for example 2-propenyl, 2-butenyl or 1-methyl-2-propenyl.

The term "alkynyl"—in isolation or as part of a chemical group—represents straight-chain or branched hydrocarbons, preferably with 2 bis 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Alkynyls with 2 to 4 carbon atoms are preferred, for example ethynyl, 2-propynyl or 2-butynyl-2-propenyl.

The term "cycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl.

The term "heterocyclyl"—in isolation or as part of a chemical group—represents saturated or partially unsaturated mono-, bi- or tricyclic hydrocarbons, preferably 3 to 10 carbon atoms, which have at least one carbon atom replaced by a heteroatom selected from O, N and S, for example tetrahydrofuran, pyrrolidine, tetrahydrothiophene.

The term "aryl" represents a mono-, bi- or polycyclical aromatic system with preferably 6 to 14, more preferably 6 to 10 ring-carbon atoms, for example phenyl, naphthyl, anthryl, phenanthrenyl, preferably phenyl. "Aryl" also represents polycyclic systems, for example tetrahydronaphtyl, indenyl, indanyl, fluorenyl, biphenyl. Arylalkyls are examples of substituted aryls, which may be further substituted with the same or different substituents both at the aryl or alkyl part. Benzyl and 1-phenylethyl are examples of such arylalkyls.

The term "heteroaryl" represents heteroaromatic groups, i.e. completely unsaturated aromatic heterocyclic groups, which fall under the above definition of heterocycles. "Heteroaryls" with 5 to 7-membered rings with 1 to 3, preferably 1 or 2 of the same or different heteroatoms selected from N, O, and S. Examples of "heteroaryls" are furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl.

The term "halogen" or "halo" represents fluoro, chloro, bromo or iodo, particularly fluoro, chloro or bromo. The chemical groups which are substituted with halogen, for example haloalkyl, halocycloalkyl, haloalkyloxy, haloalkylsulfanyl, haloalkylsulfinyl or haloalkylsulfonyl are substituted one or up to the maximum number of substituents with halogen. If "alkyl", "alkenyl" or "alkynyl" are substituted with halogen, the halogen atoms can be the same or different and can be bound at the same carbon atom or different carbon atoms.

The term "enantiomerically enriched" means that one of the enantiomers of the compound is present in excess in comparison to the other enantiomer. This excess will hereafter be referred to as enantiomeric excess or ee. The ee may be determined by chiral GC or HPLC analysis. The ee is equal to the difference between amounts of enantiomers divided by the sum of the amounts of the enantiomers, which quotient can be expressed as a percentage after multiplication with 100.

EXPERIMENTAL

Examples

The following examples are intended to illustrate the invention and are not to be construed as being limitations thereon.
Instrumentation
HPLC Methods
Method 1
HPLC apparatus: Thermo Electron Corporation; SpectraSystem P200,
SpectraSystemAS1000 and SpectraSystem UV1000.
Column: CHIRALPAK IA-3, 3 µm, 4.6 mm×100 mm.
Temperature: room temperature (rt.)
Mobile phase: EtOH+0.1 diethylamine/MeOH+0.1% diethylamine (50/50).
Flow rate: 1.0 ml/min.
Gradient: isocratic.
Detection: 223 nm.
Size of sample: 10 µL.
Rt (retention time) (1S,2S)-2-(2,4-dichlorophenyl)cyclo-butaneamine: 4.8 min.
Rt (1R,2R)-2-(2,4-dichlorophenyl)cyclo-butaneamine: 3.0 min.
Method 2
HPLC apparatus: Agilent Technologies 1260 Infinity.
Column: Agilent XDB-C18, 1.8 µm, 4.6×50 mm.
Temperature: rt
Mobile phase: A: Acetonitrile; B: MeOH; C: $H_2O$+0.1% $H_3PO_4$.
Flow rate: 1.5 mL/min.
Gradient:

| Time [min] | A [%] | B [%] | C [%] |
| --- | --- | --- | --- |
| 0.00 | 5.0 | 82.5 | 12.5 |
| 0.50 | 5.0 | 82.5 | 12.5 |
| 7.00 | 85.0 | 2.5 | 12.5 |
| 9.00 | 5.0 | 82.5 | 12.5 |

Detection: 220 nm.
Size of sample: 1 µL.
Rt of cis-isomer of 2-(2,4-dichlorophenyl)cyclobutaneamine: 2.8 min.
Method 3
HPLC apparatus: Agilent Technologies 1200 Series.
Column: Phenomenex Kinetex XB C18, 2.6 µm, 4.6×150 mm.
Temperature: 40° C.
Mobile phase: A: $H_2O$+0.1% (v/v) $H_3PO_4$; B: Acetonitrile.
Flow rate: 1.0 mL/min.
Gradient:

| Time [min] | A [%] | B [%] |
| --- | --- | --- |
| 0.0 | 70 | 30 |
| 15.0 | 50 | 50 |
| 20.0 | 10 | 90 |
| 25.0 | 10 | 90 |
| 25.1 | 70 | 30 |
| 33.0 | 70 | 30 |

Detection: 223 nm.
Size of sample: 5 µL.
Rt of cis-isomers of N-[2-(2,4-dichlorophenyl)cyclobutyl]acetamide: 9.2 min.
Method 4
HPLC apparatus: Agilent Technologies 1200 Series.
Column: CHIRALPAK IA-3, 3 µm, 4.6 mm×100 mm.
Temperature: rt.
Mobile phase: n-hexane/ethanol (98/2).
Flow rate: 1.0 ml/min.
Gradient: isocratic.
Detection: 223 nm.
Size of sample: 5 µL.
Rt N-[(1S,2S)-2-(2,4-dichlorophenyl)cyclobutyl]acetamide: 12.4 min.
Rt N-[(1R,2R)-2-(2,4-dichlorophenyl)cyclobutyl]acetamide: 15.6 min.
First Aspect:
Reaction (a1) of Scheme 1:

Example 1.1

1-(2,4-dichlorophenyl)cyclopropanecarbonitrile (1.0 g, 4.61 mmol) and trifluroroacetic acid (6 mL) were added to a 50-mL flame-dried two-necked flask which was equipped with a vacuum connection, a twin pressure balloon and a magnetic stirring bar. The reaction flask was evacuated and the vacuum was released with nitrogen twice. Then palladium, 5% on peat carbon, 50% water (50 mg, 0.013 mmol) was added to the reaction flask and the flask was purged with nitrogen before the hydrogen balloon was attached. The reaction mixture was stirred at rt (room temperature) for 2 to 4 h. Hydrogen was released and the reaction flask was purged with nitrogen once the conversion was >98%. The reaction mass was filtered under an atmosphere of nitrogen. Trifluoroacetic acid was distilled off under reduced pressure and the residue was diluted with MTBE and washed with water. The phases were separated and the lower aqueous phase was extracted twice with MTBE. The combined organic layers were washed with water and concentrated under reduced pressure to obtain 1-(2,4-dichlorophenyl)cyclopropanecarbaldehyde (1.1 g) as an oil.
$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Example 1.2

1-(2,4-dichlorophenyl)cyclopropanecarbonitrile (9.49 g, 44.0 mmol), trifluoroacetic acid (70 g), water (4.7 g) and palladium, 5% on carbon, 50% water (300 mg, 0.15 mol %) were added to a 100 mL reactor which was equipped with a vacuum connection, a nitrogen inlet and a valve connected to a hydrogen inlet. The reactor was evacuated and the vacuum was replaced with nitrogen thrice. The same procedure was repeated with $H_2$ and the reaction mixture was then stirred for 2 hours at 5° C. under 1.5 bar $H_2$ pressure. After the conversion was complete, hydrogen was released and the flask was purged with nitrogen. The reaction mixture was filtered through a pad of celite (washed with TFA) and the filtrate was concentrated under reduced pressure, diluted in toluene and washed with water twice. The resulting organic layer was concentrated under reduced pressure to afford 1-(2,4-dichlorophenyl)cyclopropanecarbaldehyde (4.2 g) as a clear brown oil.

$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Reaction (a2) of Scheme 1:

Example 2.1

1-(2,4-dichlorophenyl)cyclopropanecarbonitrile (1.0 g, 4.64 mmol), acetic acid (17.5 mL) and water (5 ml) were added to a 50 mL flame-dried two-necked flask which was equipped with a vacuum connection, a twin pressure balloon and a magnetic stirring bar. The reaction flask was evacuated and the vacuum was released with nitrogen twice. Then, Raney Nickel (50% strength w/w) with 50% water (201 mg, 0.71 mmol) was added to the reaction flask and the flask was purged with nitrogen before the hydrogen balloon was attached. The reaction mixture was stirred at rt for 6 to 10 h. Hydrogen was released and the reaction flask was purged with nitrogen once the conversion was >98%. The reaction mass was filtered through a bed of celite under an atmosphere of nitrogen. The filtrate was acidified with concentrate aqueous HCl to pH 1.0 and diluted with water and ethyl acetate. The organic layer was extracted with a 15% aqueous sodium carbonate solution and subsequently water. The solvent was removed under reduced pressure to obtain 1-(2,4-dichlorophenyl)cyclopropanecarbaldehyde (0.81 g) as an oil.

$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Example 2.2

DCP-nitrile (9.50 g, 44.0 mmol), trifluoroacetic acid (70 g), water (7.0 g) and Raney Nickel (520 mg, 20 mol %) were added to a 100 mL reactor which was equipped with a vacuum connection, a nitrogen inlet and a valve connected to a $H_2$ inlet. The reactor was evacuated and the vacuum was replaced with nitrogen thrice. A $H_2$ partial pressure of 0.5 bar was then applied and the reaction mixture was stirred at 20° C. After the conversion was complete, $H_2$ was released and the flask was purged with nitrogen. The reaction mixture was filtered through a pad of celite (washed with TFA) and the filtrate was concentrated under reduced pressure, diluted in toluene and washed with water. The resulting organic layer was concentrated under reduced pressure to afford DCP-aldehyde (7.4 g) as a slightly yellow oil.

$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Reaction (a3) of Scheme 1:

Example 3

A 1.2 M solution of DIBAL in toluene (75.2 g, 105 mmol) was added to a solution of 1-(2,4-dichlorophenyl)cyclopropanecarbonitrile (20 g, 91.5 mmol) in toluene (40 g) in a way that the temperature was kept between −5° C. and 0° C. After a post addition stirring period of 30 minutes, a 2 M aqueous HCl-solution was added to the reaction mixture at −20° C. Subsequently, the reaction mixture was allowed to reach rt. The reaction mixture was diluted with ethyl acetate and extracted with water. The phases were separated and the aqueous phase was extracted twice with ethyl acetate. The combined organic phases were extracted with water and brine, dried over $Na_2SO_4$, filtered and the solvents were removed under reduced pressure. 1-(2,4-dichlorophenyl)cyclopropanecarbaldehyde (20.1 g) was isolated as a yellow oil.

$^1$H NMR (400 MHz, CDCl$_3$) δ 9.05 (s, 1H), 7.45 (m, 1H), 7.20 (m, 2H), 1.70 (m, 2H), 1.40 (m, 2H).

Reaction (a4) of Scheme 1:

Example 4.1

A 60% solution of REDAL in toluene (87.6 g, 260 mmol) was dosed over 4 h to a solution of 1-(2,4-dichlorophenyl)cyclopropanecarbonitrile (84.8 g, 400 mmol) in toluene (212 g) at a temperature of 0° C. After a post addition stirring period of 2 hours at 0° C., the reaction mixture was dosed onto a 50% aqueous acetic acid solution (384 g, 3.2 mol) in a way to keep temperature of the reaction mixture below <25° C. Subsequently, a 32% aqueous HCl solution (137 g, 1.2 mol) was dosed to the mixture. The phases were separated and the organic phase was extracted twice with water (75 g) before the solvent of the organic phase was removed under reduced pressure. 1-(2,4-dichlorophenyl)cyclopropanecarbaldehyde (81.0 g) was isolated as an orange oil.

$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Example 4.2

A 70% solution of REDAL in toluene (97.3 g, 0.34 mol) was dosed over 80 minutes to a solution of 1-(2,4-dichlorophenyl)cyclopropanecarbonitrile (120.0 g, 0.54 mmol) in toluene (182 g) at a temperature of 20-25° C. After a post addition stirring period of 1 h at 20-25° C., the reaction mixture was dosed onto a mixture consisting of a 50% aqueous acetic acid solution (266.0 g, 2.19 mol) and a 35% aqueous HCl solution (160.0 g, 1.54 mol) keeping the temperature of the reaction mixture below 25° C. The phases were separated and the organic phase was extracted twice with water (60 g) before the solvent of the organic phase was removed under reduced pressure. 1-(2,4-dichlorophenyl)cyclopropanecarbaldehyde (118.4 g) was isolated as a dark orange oil.

$^1$H NMR (400 MHz, DMSO-$d_6$) δ 8.75 (s, 1H), 7.60 (d, J=1.90 Hz, 1H), 7.46-7.27 (m, 2H), 1.80-1.61 (m, 2H), 1.47-1.36 (m, 2H).

Second Aspect:
Reaction (b) of Scheme 1:

Example 5.1

To a 10-mL flame-dried two-necked flask, equipped with a thermometer and a bubbler, under argon, containing 1-(2,4-dichlorophenyl)cyclopropanecarbaldehyde (1.4 g, 6.0 mmol), was added chlorobenzene (6 mL), followed by anhydrous AlCl$_3$ (1.2 g, 9.0 mmol). The resulting suspension was heated 1 h at 45° C.

After cooling down to rt, the mixture was poured on cold 1N HCl and diluted with ethyl acetate. The aqueous phase was extracted twice with dichloromethane. The combined organic phase was washed once with 1N HCl and once with brine then dried with solid $Na_2SO_4$, filtered and concentrated under vacuum. 2-(2,4-dichlorophenyl)cyclobutanone (1.35 g) was isolated as a brown oil.

$^1$H NMR (400 MHz, CDCl$_3$) δ 7.40 (d, J=2.2 Hz, 1H), 7.30 (d, J=8.1 Hz, 1H), 7.21 (dd, J=2.2 and 8.4 Hz, 1H), 4.76 (m, 1H), 3.25 (m, 1H), 3.10 (m, 1H), 2.63 (m, 1H), 2.12 (m, 1H).

Example 5.2

A solution of 1-(2,4-dichlorophenyl)cyclopropanecarbaldehyde (109.9 g, 0.5 mol) in 1,2-dichlorobenzene (64.8 g, 0.44 mol) was added over 90 minutes to a suspension of AlCl$_3$ (87.6 g, 0.65 mol) in 1,2-dichlorobenzene (100.0 g, 0.68 mol) at Ti=50-55° C.; the suspension was purged with a light stream of nitrogen during the dosing and the post addition stirring period. Essentially complete conversion was achieved after a post addition stirring period of 1 h at Ti=50-55° C. The reaction mixture was cooled to rt and then dosed onto a 14% aqueous HCl-solution (352.7 g, 1.34 mol) in a way that Ti was kept below 40° C. The mixture was stirred for 45 minutes before the phases were separated. The organic phase was subsequently extracted twice with water (83.3 g, 4.6 mol and 80.0 g, 4.4 mol) before the organic phase was concentrated under reduced pressure. 2-(2,4-dichlorophenyl)cyclobutanone (110.6 g) was isolated as a brown oil.

$^1$H NMR (400 MHz, CDCl$_3$) δ 7.40 (d, J=2.2 Hz, 1H), 7.30 (d, J=8.1 Hz, 1H), 7.21 (dd, J=2.2 and 8.4 Hz, 1H), 4.76 (m, 1H), 3.25 (m, 1H), 3.10 (m, 1H), 2.63 (m, 1H), 2.12 (m, 1H).

Examples 6-9

The following compounds were prepared in an analogous manner to example 5:

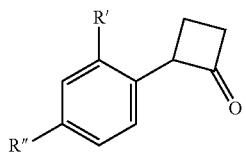

TABLE 1

| Example | R' | R" | $^1$H NMR (400 MHz, CDCl$_3$) |
|---|---|---|---|
| 6 | H | Cl | 7.31-7.10 (m, 4H), 4.50 (m, 1H), 3.22 (m, 1H), 3.02 (m, 1H), 2.55 (m, 1H), 2.18 (m, 1H). |
| 7 | F | F | 7.22 (m, 1H), 6.80 (m, 2H), 4.55 (m, 1H), 3.25 (m, 1H), 3.09 (m, 1H), 2.53 (m, 1H), 2.13 (m, 1H). |
| 8 | Br | Cl | 7.35 (m, 2H), 6.95 (m, 1H), 4.75 (m, 1H), 3.25 (m, 1H), 3.06 (m, 1H), 2.63 (m, 1H), 2.06 (m, 1H). |
| 9 | Cl | F | 7.30 (m, 1H), 7.10 (m, 1H), 6.90 (m, 1H), 4.69 (m, 1H), 3.19 (m, 1H), 2.98 (m, 1H), 2.53 (m, 1H), 2.06 (m, 1H). |

Third Aspect:
Reaction (c) of Scheme 1:

Examples 10-18

A pressure autoclave was charged with 2-(2,4-dichlorophenyl)cyclobutanone (0.5 mmol), [RuCl(p-cymene)((S)-DM-SEGPHOS)]Cl (0.005 mmol), the corresponding ammonium salt (0.5 mmol, see Table 2) and MeOH (5 mL). A hydrogen pressure of 30 bar was applied and the reaction mixture was heated to 80° C. After a stirring period of 22 h the reaction mixture was cooled to rt and analyzed via chiral HPLC (method 1) and $^1$H NMR.

TABLE 2

| Example | Ammonium salt | Yield [%] | ee [%] (S,S) |
|---|---|---|---|
| 10 | Ammonium acetate | 79 | 83 |
| 11 | Ammonium benzoate | 94 | 74 |
| 12 | Ammonium salicylate | 85 | 76 |
| 13 | Ammonium o-chlorobenzoate | 79 | 78 |
| 14 | Ammonium m-chlorobenzoate | >99 | 72 |
| 15 | Ammonium p-methoxybenzoate | 84 | 73 |
| 16 | Ammonium chloroacetate | n.d. | 83 |
| 17 | Ammonium dichloroacetate | 19 | n.d. |
| 18 | Ammonium trichloroacetate | 13 | n.d. | n.d. = not determined

Examples 19-24

A pressure autoclave was charged with 2-(2,4-dichlorophenyl)cyclobutanone (0.5 mmol), [RuCl(p-cymene)((S)-DM-SEGPHOS)]Cl (0.005 mmol), the corresponding ammonium salt (0.6 mmol, see Table 3) and MeOH (2.5 mL). A hydrogen pressure of 30 bar was applied and the reaction mixture was heated to 80° C. The reaction mixture was cooled to rt after a stirring period of 18.5 h and H$_2$O (20 mL) and HCl (1M, 2 mL) were added. The mixture was extracted with MTBE (20 mL) and the organic layer was extracted with an aqueous HCl-solution (2 ml HCl 1M and 20 mL H$_2$O). The aqueous phase was basified using an aqueous NaOH-solution (5 M, 2 mL) and it was extracted with MTBE (3×20 mL). The combined organic layers were dried over Na$_2$SO$_4$, filtered and the solvent was removed under reduced pressure. The residue was analyzed via chiral HPLC (method 1) and $^1$H NMR.

TABLE 3

| Example | Ammonium salt | Yield [%] | ee [%] (S,S) |
|---|---|---|---|
| 19 | Ammonium p-chlorobenzoate | 58 | 70 |
| 20 | Ammonium hydroxyacetate | 58 | 86 |

TABLE 3-continued

| Example | Ammonium salt | Yield [%] | ee [%] (S,S) |
|---|---|---|---|
| 21 | Ammonium lactate | 57 | 80 |
| 22 | Ammonium (S)-lactate | 40 | 80 |
| 23 | Ammonium methoxyacetate | 72 | 82 |
| 24 | Ammonium 2-acetoxyacetate | 60 | 84 |

Example 25-26

A 7N ammonia solution in MeOH (108 mmol) was added to a mixture of the corresponding acid (110 mmol) in MeOH (as much to get a 10% solution of the ammonium salt) at rt. The mixture was stirred for about 10 minutes and was ready to be used in the direct asymmetric reductive amination step.
Direct Asymmetric Reductive Amination A pressure autoclave was charged with $[NH_2Me_2][(RuCl((R)\text{-xylbinap}))_2(u\text{-Cl})_3]$ (0.135 mmol), the previously prepared 10% solution of the corresponding ammonium salt in MeOH (108 mmol, see Table 4) and MeOH (44 g). The reaction mixture was heated to 80° C. and a hydrogen pressure of 30 bar was applied. Subsequently, a solution of 2-(2,4-dichlorophenyl)cyclobutanone (624 mmol) in MeOH (20 g) was added over 4 h to the autoclave. The reaction mixture was cooled to rt after the post addition stirring period of 2 h. Subsequently, the reaction mixture was basified and analyzed via chiral (method 1) and achiral (method 2) HPLC.

TABLE 4

| Example | Ammonium salt | Yield [%] | ee [%] (S,S) |
|---|---|---|---|
| 25 | Ammonium phenoxyacetate | 73 | 84 |
| 26 | Ammonium furan-2-carboxylate | 73 | 77 |

Examples 27-46

Different additives were tested in a screening platform. The reaction vessel was charged with 2-(2,4-dichlorophenyl)cyclobutanone (2.0 mmol), $[NH_2Me_2][(RuCl((R)\text{-xylbinap}))_2(u\text{-Cl})_3]$ (0.25 mol %), ammonium acetate (2.4 mmol), the corresponding additive (see Table 5) and MeOH (2.5 mL). A hydrogen pressure of 30 bar was applied and the reaction mixture was heated to 80° C. After a stirring period of 16 h the reaction mixture was cooled to rt and analyzed via via chiral (method 1) and achiral (method 2) HPLC.

TABLE 5.1

| Example | Additive | Additive [Eq] | Yield [%] | ee [%] (S,S) |
|---|---|---|---|---|
| 27 | None | n.a. | 68 | 73 |
| 28 | Chloroacetic acid | 1.0 | 67 | 70 |
| 29 | Chloroacetic acid | 0.1 | 77 | 74 |
| 30 | Trifluoroacetic acid | 1.0 | 36 | 74 |
| 31 | Trifluoroacetic acid | 0.1 | 76 | 71 |
| 32 | Methoxyacetic acid | 1.0 | 81 | 71 |
| 33 | Methoxyacetic acid | 0.1 | 77 | 74 |
| 34 | Salicylic acid | 1.0 | 55 | 61 |
| 35 | Salicylic acid | 0.1 | 74 | 75 |
| 36 | 2-methoxybenzoic acid | 1.0 | 46 | 67 |
| 37 | 2-methoxybenzoic acid | 0.1 | 71 | 74 |
| 38 | N-methylglycine | 1.0 | 33 | 80 |
| 39 | N-methylglycine | 0.1 | 67 | 76 |
| 40 | HOAc | 1.0 | 80 | 70 |
| 41 | $NH_4Br$ | 0.1 | 75 | 77 |
| 42 | Iodine | 0.1 | 75 | 80 |
| 43 | 2,2,2-Trifluoroethanol | 1.0 | 77 | 75 |
| 44 | 2,2,2-Trifluoroethanol | 0.1 | 75 | 75 |
| 45 | $MgSO_4$ | | 61 | 71 |
| 46 | Molecular sieve | | 73 | 75 |

Examples 46.1, 46.2

A pressure autoclave was charged with 2-(2,4-dichlorophenyl)cyclobutanone (93.0 mmol), $[NH_2Me_2][(RuCl((R)\text{-xylbinap}))_2(u\text{-Cl})_3]$ (0.1 mol %), ammonium phenoxyacetate (158.4 mmol), the corresponding additive (see Table 5.2) and MeOH (4.1 mol). A hydrogen pressure of 30 bar was applied and the reaction mixture was heated to 80° C. After a stirring period of 17 h the reaction mixture was cooled to rt and analyzed via chiral (method 1) and achiral (method 2) HPLC.

TABLE 5.2

| Example | Additive | Additive [Eq] | Yield [%] | ee [%] (S,S) |
|---|---|---|---|---|
| 46.1 | $NH_4Cl$ | 0.1 | 69 | 82 |
| 46.2 | Phenoxyacetic acid | 0.25 | 71 | 83 |

Examples 47-51

A pressure autoclave was charged with 2-(2,4-dichlorophenyl)cyclobutanone (0.5 mmol), [RuCl(p-cymene)((S)-DM-SEGPHOS)]Cl (0.005 mmol), ammonium acetate (0.6 mmol) and the corresponding solvent (5.0 mL). A hydrogen pressure of 30 bar was applied and the reaction mixture was heated to 80° C. The reaction mixture was cooled to rt after a stirring period of 19 h and $H_2O$ (20 mL) and a 1M aqueous HCl-solution (2 mL) were added. The mixture was extracted with MTBE (20 mL) and the organic layer was extracted with an aqueous HCl-solution (2 ml HCl 1M and 20 mL $H_2O$). The aqueous phase was basified using an aqueous 5M NaOH-solution (2 mL) and it was extracted with MTBE (3×20 mL). The combined organic layers were dried over $Na_2SO_4$, filtered and the solvent was removed under reduced pressure. The residue was analyzed via chiral HPLC (method 1) and $^1$H NMR.

TABLE 6

| Example | Solvent | Yield [%] | ee [%] (S,S) |
|---|---|---|---|
| 47 | MeOH | 67 | 81 |
| 48 | $CF_3CH_2OH$ | 38 | 55 |
| 49 | EtOH | 61 | 74 |
| 50 | $CH_2Cl_2$ | 60 | 57 |
| 51 | Toluene | 17 | 63 |

Examples 52

A pressure autoclave was charged with 2-(2,4-dichlorophenyl)cyclobutanone (1.4 mmol), [RuCl(p-cymene)((S)-DM-SEGPHOS)]Cl (0.014 mmol), ammonium metachlorbenzoate (1.4 mmol) and MeOH (13.8 mL). A hydrogen pressure of 5 bar was applied and the reaction mixture was heated to 80° C. The reaction mixture was cooled to rt after a stirring period of 16 h. $H_2O$ (50 mL) and a 1M aqueous HCl-solution (5 mL) were added. The mixture was extracted with MTBE (50 mL) and the organic layer was extracted with an aqueous HCl-solution (5 ml HCl 1M and 20 mL $H_2O$). The aqueous phase was basified using a 5M aqueous NaOH-solution (5 mL) and it was extracted with MTBE (3×50 mL). The combined organic layers were dried over $Na_2SO_4$, filtered and the solvent was removed under reduced pressure. The residue was analyzed via chiral HPLC (method 1) and $^1$H NMR.

Examples 53

A pressure autoclave was charged with 2-(2,4-dichlorophenyl)cyclobutanone (0.5 mmol), [RuCl(p-cymene)((S)-

DM-SEGPHOS)]Cl (0.005 mmol), ammonium metachlorbenzoate (0.5 mmol) and MeOH (5 mL). A hydrogen pressure of 10 bar was applied and the reaction mixture was heated to 80° C. The reaction mixture was cooled to rt after a stirring period of 17 h and analyzed via chiral HPLC (method 1) and $^1$H NMR.

Examples 54

A pressure autoclave was charged with 2-(2,4-dichlorophenyl)cyclobutanone (0.46 mmol), [RuCl(p-cymene)((S)-DM-SEGPHOS)]Cl (0.0046 mmol), ammonium metachlorbenzoate (0.55 mmol) and MeOH (2.3 mL). A hydrogen pressure of 10 bar was applied and the reaction mixture was heated to 80° C. The reaction mixture was cooled to rt after a stirring period of 19 h. H$_2$O (20 mL) and a 1M aqueous HCl-solution (2 mL) were added. The mixture was extracted with MTBE (20 mL) and the organic layer was extracted with an aqueous HCl-solution (2 ml HCl 1M and 20 mL H$_2$O). The aqueous phase was basified using a 5M aqueous NaOH-solution (2 mL) and it was extracted with MTBE (3×20 mL). The combined organic layers were dried over Na$_2$SO$_4$, filtered and the solvent was removed under reduced pressure. The residue was analyzed via chiral HPLC (method 1) and $^1$H NMR.

The results of examples 52-54 are summarized in table 7.

TABLE 7

| Example | H$_2$ Pressure [Bar] | Reaction time [h] | Yield [%] | ee [%] (S,S) |
|---|---|---|---|---|
| 52 | 5 | 16 | 70 | 70 |
| 53 | 10 | 17 | 73 | 71 |
| 54 | 30 | 19 | 69 | 69 |

Examples 55-56

A pressure autoclave was charged with 2-(2,4-dichlorophenyl)cyclobutanone (4.0 mmol), Ru(OAc)$_2$[(R)-xylbinap] (0.02 mmol), ammonium acetate (4.8 mmol), acetic acid (6.4 mmol) and MeOH (10 mL). A hydrogen pressure of 30 bar was applied and the reaction mixture was heated to 80° C. After the corresponding stirring period the reaction mixture was cooled to rt. The mixture was diluted with MTBE and water and a 1M HCl-solution was added. The organic phase was extracted twice with a 1M HCl solution. The combined aqueous phases were basified using an aqueous 5M NaOH-solution and it was extracted three time with MTBE. The combined organic layers were dried over Na$_2$SO$_4$, filtered and the solvent was removed under reduced pressure. The residue was analyzed via chiral HPLC (method 1) and $^1$H NMR.

TABLE 8

| Example | T [° C.] | Reaction time [h] | Yield [%] | ee [%] (S,S) |
|---|---|---|---|---|
| 55 | 50 | 16 | 18 | n.d. |
| 56 | 80 | 4 | 76 | 75 |

Examples 57-66

Different preformed Ru-catalysts were tested in a screening platform. The reaction vessel was charged with 2-(2,4-dichlorophenyl)cyclobutanone (2.0 mmol), the corresponding catalyst (see Table 9), ammonium acetate (2.4 mmol) and MeOH (2.5 mL). A hydrogen pressure of 30 bar was applied and the reaction mixture was heated to 80° C. After a stirring period of 16 h the reaction mixture was cooled to rt and analyzed via chiral (method 1) and achiral (method 2) HPLC.

TABLE 9

| Example | Catalyst | Catalyst loading [mol %] | Yield [%] | ee [%] (S,S) |
|---|---|---|---|---|
| 57 | [NH$_2$Me$_2$][(RuCl((R)-xylbinap))$_2$(μ-Cl)$_3$] | 0.25 | 68 | 73 |
| 58 | [NH$_2$Me$_2$][(RuCl((R)-xylbinap))$_2$(μ-Cl)$_3$] | 0.125 | 57 | 74 |
| 59 | Ru(OAc)$_2$[(R)-xylbinap] | 0.25 | 58 | 73 |
| 60 | Ru(OAc)$_2$[(R)-xylbinap] | 0.125 | 20 | 72 |
| 61 | [RuCl(p-cymene)((R)-xylbinap)]Cl | 0.25 | 70 | 75 |
| 62 | [RuCl(p-cymene)((R)-xylbinap)]Cl | 0.125 | 53 | 74 |
| 63 | RuCl$_2$[(R)-xylbinap][(R)-daipen] | 0.25 | 60 | 75 |
| 64 | RuCl$_2$[(R)-xylbinap][(R)-daipen] | 0.125 | 20 | 73 |
| 65 | RuCl$_2$[(R)-xylbinap][(R,R)-dpen] | 0.25 | 74 | 75 |
| 66 | RuCl$_2$[(R)-xylbinap][(R,R)-dpen] | 0.125 | 58 | 74 |

Examples 67-93

Different chiral ligands in combination with ruthenium were tested in a screening platform. [Ru(Me-allyl)$_2$(cod)] and the corresponding ligand (see Table 10) were dissolved in acetone (2.5 ml) and subsequently stirred for 1 h at 25° C. The mixture was evaporated to dryness, MeOH was added and the catalyst solution (0.25 mol %) was transferred into the autoclave together with 2-(2,4-dichlorophenyl)cyclobutanone (2.0 mmol), ammonium acetate (2.4 mmol) and MeOH (2.5 mL). A hydrogen pressure of 30 bar was applied and the reaction mixture was heated to 80° C. After a stirring period of 16 h the reaction mixture was cooled to rt and analyzed via chiral (method 1) and achiral (method 2) HPLC.

TABLE 10

| Example | Ligand | Yield [%] | ee [%] |
|---|---|---|---|
| 67 | (R)-(−)-5,5'-Bis[di(3,5-di-tert-butyl-4-methoxyphenyl)phosphino]-4,4'-bi-1,3-benzodioxole | 27.0 | 66.5 (S,S) |
| 68 | (S)-1,13-Bis(diphenylphosphino)-7,8-dihydro-6H-dibenzo[f,h][1,5]dioxonin | 20.4 | 64.2 (S,S) |
| 69 | (S,S)Fc-1,1'-Bis[bis(3,5-dimethylphenyl)phosphino]-2,2'-bis[(R,R)C-(N,N-dimethylamino)phenylmethyl]ferrocene | 20.7 | 67.7 (S,S) |

TABLE 10-continued

| Example | Ligand | Yield [%] | ee [%] |
|---|---|---|---|
| 70 | (R)-2,2'-Bis[bis(3,5-diisopropyl-4-dimethylaminophenyl)phosphino]-6,6'-dimethoxy-1,1'-biphenyl | 35.3 | 63.1 (S,S) |
| 71 | (S)-2,2'-Bis[bis(3,4,5-trimethoxyphenyl)phosphino]-4,4',5,5',6,6'-hexamethoxy-1,1'-biphenyl | 14.0 | 78.2 (R,R) |
| 72 | (R)-(+)-2,2'-Bis[di(3,5-xylyl) phosphino]-1,1'-binaphthyl | 50.9 | 74.1 (S,S) |
| 73 | (R)-1-Diphenylphosphino-2-[(R)-(N,N-dimethylamino)[2-(diphenylphosphino)phenyl]methyl]ferrocene | 32.9 | 16.6 (S,S) |
| 74 | (R)-(+)-2,2'-Bis(diphenylphosphino)-5,5',6,6',7,7',8,8'-octahydro-1,1'-binaphthyl | 65.8 | 73.5 (S,S) |
| 75 | (R)-1-[(R)-1-[Bis[3,5-bis(trifluoromethyl)phenyl]phosphino]ethyl]-2-[2-(diphenylphosphino)phenyl]ferrocene | 49.5 | 88.8 (R,R) |
| 76 | (R)-2,2'-Bis[bis(3,5-di-tert-butyl-4-methoxyphenyl)phosphino]-6,6'-dimethoxy-1,1'-biphenyl | 16.4 | 71.5 (S,S) |
| 77 | (S)-2,2'-Bis[di-3,5-xylylphosphino]-6,6'-dimethoxy-1,1'-biphenyl | 43.9 | 73.7 (R,R) |
| 78 | (R)-(+)-2,2',6,6'-Tetramethoxy-4,4'-bis(di(3,5-xylyl)phosphino)-3,3'-bipyridine | 47.3 | 76.7 (S,S) |
| 79 | (R)-1-[(R)-1-(Diphenylphosphino)ethyl]-2-[2-(diphenylphosphino)phenyl]ferrocene | 69.4 | 34.6 (R,R) |
| 80 | (S)-2,2'-Bis(di-p-dimethylaminophenylphosphino)-6,6'-dimethoxy-1,1'-biphenyl | 17.3 | 46.5 (R,R) |
| 81 | (R)-2,2'-Bis[bis(3,5-di-tert-butylphenyl)phosphino]-6,6'-dimethoxy-1,1'-biphenyl | 26.2 | 70.8 (S,S) |
| 82 | (S)-(-)-6,6'-Bis(diphenylphosphino)-2,2',3,3'-tetrahydro-5,5'-bi-1,4-benzodioxin | 24.4 | 69.0 (R,R) |
| 83 | (R)-1-[(R)-1-[Di(3,5-xylyl)phosphino]ethyl]-2-[2-[di(3,5-xylyl)phosphino]phenyl]ferrocene | 63.6 | 50.5 (R,R) |
| 84 | (R)-2,2'-Bis(diphenylphosphino)-6,6'-dimethoxy-1,1'-biphenyl | 24.4 | 69.6 (S,S) |
| 85 | (S)-2,2'-Bis(di-m-dimethylaminophenylphosphino)-6,6'-dimethoxy-1,1'-biphenyl | 39.2 | 63.8 (S,S) |
| 86 | (R)-2,2'-Bis[bis(3,5-diisopropyl-4-dimethoxyphenyl)phosphino]-6,6'-dimethoxy-1,1'-biphenyl | 19.4 | 68.2 (S,S) |
| 87 | (R)-(+)-5,5'-Bis[di(3,5-xylyl)phosphino]-4,4'-bi-1,3-benzodioxole | 43.7 | 72.9 (S,S) |
| 88 | (+)-1,2-Bis[(2R,5R)-2,5-diisopropylphospholano]benzene | 71.9 | 11.2 (R,R) |
| 89 | (S)-2,2'-Bis(di-p-tolylphosphino)-6,6'-dimethoxy-1,1'-biphenyl | 18.9 | 65.9 (R,R) |
| 90 | (S)-2,2'-Bis(di-6-methoxy-2-naphthalenylphosphino)-6,6'-dimethoxy-1,1'-biphenyl | 14.7 | 75.8 (R,R) |
| 91 | (R)-2,2'-Bis[bis(3,5-diisopropylphenyl)phosphino]-6,6'-dimethoxy-1,1'-biphenyl | 15.4 | 67.0 (S,S) |
| 92 | 1-Dicyclohexylphosphino-1'-[(S)$_P$-[(S)$_{Fc}$-2-[(R)$_C$-1-(dimethylamino)ethyl]ferrocenyl]phenylphosphino]ferrocene | 17.6 | 44.7 (S,S) |
| 93 | (S)-(−)-5,5'-Bis(diphenylphosphino)-2,2,2',2'-tetrafluoro-4,4'-bi-1,3-benzodioxole | 15.6 | 75.2 (R,R) |

Example 94

A solution of ammonium methoxyacetate in MeOH (323 g, 301 mmol), methanol (123 g), diacetato((R)-(+)-2,2'-bis[di(3,5-xylyl)phosphino]-1,1'-binaphthyl) ruthenium (0.72 g, 0.75 mmol) were charged to a pressure reactor. The reactor was sealed and 3 pressure swings to $N_2$ (6 bar) without stirring followed by 3 pressure swings to $H_2$ (6 bar) with stirring were carried out and the mixture was heated to 55° C. The pressure was increased to 10 bar using hydrogen and the reactor heated to 80° C. At 80° C., the pressure was increased to 30 bar. A solution of 2-(2,4-dichlorophenyl)cyclobutanone in MeOH (110 g, 249 mmol) was added to the reactor over 4 h. The reaction mixture was stirred for 8 h, until the hydrogen uptake had stopped. The pressure was released and 3 pressure swings to $N_2$ (6 bar) were carried out. The reaction mass was then concentrated in vacuo (60° C., 90 mbar) to give a brown oil.

Water (450 mL) and ethyl acetate (300 mL) were added to the crude product. A 32% aqueous HCl solution (37.5 g) was added to reach pH 1 and the phases were left to separate. The lower aqueous phase was removed and the upper organic phase was washed with a 1M aqueous HCl solution (50 mL) and the phases were left to separate. The lower aqueous phase was combined with the previous aqueous phase and the upper organic phase was discarded. Toluene (100 mL) was added to the combined aqueous phases and the bi-phasic system was cooled to 10° C. A 30% aqueous NaOH solution (80 g) was added to reach pH 10, keeping the temperature below 20° C. The phases were left to separate. The lower aqueous phase was removed and washed twice with toluene (2×100 mL). The combined organic and toluene layers were washed with water (100 mL) and concentrated under reduced pressure to give (1S,2S)-2-(2,4-dichlorophenyl)cyclobutanamine (45.5 g) as an oil.

$^1$H NMR (400 MHz, DMSO-d$_6$) δ 7.54 (m, 1H), 7.41 (d, J=1 Hz, 2H); 3.85-3.75 (m, 2H), 2.40-2.24 (m, 2H), 2.11-2.02 (m, 1H), 1.61-1.53 (m, 1H), 1.15 (br s, 2H).

Examples 95-98

The following compounds in Table 11 were prepared in an analogous manner to examples 10-94.

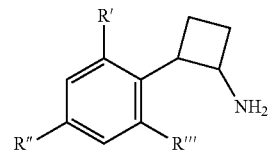

TABLE 11

| Entry | R' | R' | R''' | $^1$H NMR |
|---|---|---|---|---|
| 95 | F | F | H | $^1$H NMR (400 MHz, CDCl$_3$) δ 7.30-7.20 (m, 1H), 6.93-6.86 (m, 1H), 6.84-6.76 (m, 1H), 3.88-3.80 (m, 2H), 2.46-2.35 (m, 1H), 2.29-2.11 (m, 2H), 1.77-1.66 (m, 1H). |
| 96 | CF$_3$ | H | H | $^1$H NMR (400 MHz, CDCl$_3$) δ 7.69 (d, J = 7.7 Hz, 1H), 7.63-7.56 (m, 2H), 7.38-7.32 (m, 1H), 4.13-4.05 (m, 1H), 3.92-3-85 (m, 1H), 2.52-2.34 (m, 2H), 2.29-2.19 (m, 1H), 1.85-1.74 (m, 1H). |
| 97 | F | CF$_2$H | H | $^{19}$F NMR (400 MHz, DMSO-d$_6$) δ −109.7, −114.1. |
| 98 | F | F | F | $^{19}$F NMR (400 MHz, DMSO-d$_6$) δ −135.6 (d, J = 21Hz, 2F), −164.3 (t, J = 21 Hz, 1F). |

Fourth Aspect:
Reaction (d) of Scheme 1:

Example 99

To a solution of 2-(2,4-dichlorophenyl)cyclobutanone (5.00 g, 23.2 mmol) in chlorobenzene (23.2 mL) were added at rt AlCl$_3$ (4.65 g, 34.9 mmol), CH$_3$CN (6.08 mL, 116 mmol) and AcCl (2.48 mL, 34.9 mmol). A slight exotherm was observed upon addition of AcCl. The resulting yellowish suspension was heated at 50° C. for 1 h. After cooling down to rt, the reaction mixture was added dropwise to a 0° C. cold aqueous solution of 4N NaOH (116 mL) and 50 mL of toluene. A pale yellow precipitate formed during addition. After filtration, N-[2-(2,4-dichlorophenyl)cyclobuten-1-yl]acetamide (3.56 g) was obtained as a white solid.

$^1$H NMR (400 MHz, DMSO-d$_6$) δ 9.30 (bs, 1H); 7.51 (s, 1H), 7.47 (m, 2H), 2.85 (m, 2H), 2.68 (m, 2H), 1.92 (s, 3H).

Examples 100-107

The following compounds in Table 12 were prepared in an analogous manner to example 99:

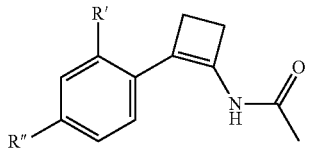

TABLE 12

| Example | R' | R'' | $^1$H NMR |
|---|---|---|---|
| 100 | H | OCF$_3$ | $^1$H NMR (400 MHz, CDCl$_3$) δ 7.30-7.13 (m, 5H), 3.05 (m, 2H), 2.57 (m, 2H), 2.1 (s, 3H). |
| 101 | H | OCHF$_2$ | $^1$H NMR (400 MHz, Acetone-d$_6$) δ 9.05 (bs, 1H), 7.38 (d, J = 8.8 Hz, 2H), 7.13 (d, J = 8.8 Hz, 2H), 6.97 (t, J = 74.5 Hz, 1H), 3.01 (t, J = 3.5 Hz, 2H), 2.55 (t, J = 3.5 Hz, 2H), 2.06 (s, 3H). |
| 102 | CF$_3$ | H | $^1$H NMR (400 MHz, CDCl$_3$) δ 7.66 (d, J = 7.7 Hz, 1H), 7.51 (t, J = 7.3 Hz, 1H), 7.38-7.30 (m, 2H), 3.05 (t, J = 2.9 Hz, 2H), 2.72 (t, J = 2.9 Hz, 2H), 2.01 (s, 3H). |
| 103 | CF$_3$ | F | $^1$H NMR (400 MHz, CDCl$_3$) δ 7.40-7.30 (m, 2H), 7.22-7.09 (m, 2H), 3.05 (t, J = 3 Hz, 2H), 2.69 (bs, 2H), 2.02 (s, 3H). |
| 104 | Br | F | $^1$H NMR (400 MHz, CDCl$_3$) δ 7.47 (bs, 1H), 7.30 (dd, J = 8.4 and 2.6 Hz, 1H), 7.19 (dd, J = 8.6 and 6.1 Hz, 1H), 7.02 (dt, J = 2.6 and 8.3 Hz, 1H), 3.03 (t, J = 3.3 Hz, 2H), 2.70 (t, J = 3.3 Hz, 2H), 2.06 (s, 3H). |
| 105 | Cl | Br | $^1$H NMR (400 MHz, CDCl$_3$) δ 7.61 (bs, 1H), 7.50 (d, J = 1.8 Hz, 1H), 7.35 (dd, J = 8.44 and 1.83 Hz, 1H), 7.08 (d, J = 8.4 Hz, 1H), 3.04 (bs, 2H), 2.67 (bs, 2H), 2.07 (s, 3H). |
| 106 | Cl | F | $^1$H NMR (400 MHz, Acetone-d$_6$) δ 8.94 (bs, 1H), 7.41 (dd, J = 8.6 and 6.4 Hz, 1H), 7.22 (dd, J = 8.8 and 2.5 Hz, 1H), 7.09 (dt, J = 2.5 and 8.4 Hz, 1H), 2.99 (t, J = 3.4 Hz, 2H), 2.74 (t, J = 3.3 Hz, 2H), 2.02 (s, 3H). |
| 107 | F | F | $^1$H NMR (400 MHz, CDCl$_3$) δ 7.73 (bs, 1H), 7.09 (dt, J = 6.6 and 8.4 Hz, 1H), 6.92-6.77 (m, 2H), 3.09 (t, J = 3.3 Hz, 2H), 2.56 (t, J = 3.5 Hz, 2H), 2.08 (s, 3H). |

Examples 108-119

N-[2-(2,4-dichlorophenyl)cyclobuten-1-yl]acetamide (a compound of formula (VI)) may be prepared in analogy to example 99 applying the reaction parameters mentioned under examples 108-119:

TABLE 13

| Example | Lewis/ Brönsted Acid (eq) | CH$_3$CN (eq) | Additive (eq) | T [° C.] | t [h] | Solvent | CC$^a$ [mol/L] | Chemical yield [%] |
|---|---|---|---|---|---|---|---|---|
| 108 | AlCl$_3$ (1.5) | 5 | p-MeOC$_6$H$_4$COCl (0.25) | 50 | 3 | C$_6$H$_5$Cl | 1 | 80% |
| 109 | FeCl$_3$ (1) | 5 | AcCl (2) | 25 | 1.25 | DCE | 0.33 | 42% |
| 110 | BF$_3$•Et$_2$O (1.5) | 5 | AcCl (2) | 40 | 18 | DCE | 0.33 | 56% |
| 111 | HBF$_4$•Et$_2$O (1.5) | 5 | AcCl (2) | 25 | 3.5 | DCE | 0.33 | 57% |
| 112 | HBF$_4$•Et$_2$O (1.5) | 5 | p-Anisic anhydride (0.5) | 50 | 18 | C$_6$H$_5$Cl | 0.5 | 46% |
| 113 | HBF$_4$•Et$_2$O (1.5) | 5 | Isopropenyl acetate (0.5) | 25 | 16 | C$_6$H$_5$Cl | 0.5 | 53% |
| 114 | Triflic Acid (1.5) | 5 | AcCl (2) | 25 | 0.5 | DCE | 0.33 | 62% |
| 115 | nonaflic acid (1.5) | 5 | AcCl (1.5) | 50 | 6 | DCE | 0.33 | 52% |
| 116 | MeSO$_3$H (5) | 5 | AcCl (2) | 30 | 16 | DCE | 0.11 | 28% |
| 117 | MeSO$_3$H (2.5) | 10 | p-Anisic anhydride (0.5) | 25 | 1 | none | — | 31% |
| 118 | Eaton's reagent (2.5) | 5 | AcCl (2) | 25 | 23 | C$_6$H$_5$Cl | 0.5 | 33% |
| 119 | Eaton's reagent (2.5) | 10 | Isopropenyl acetate (1) | 25 | 1.5 | none | — | 44% |

$^a$Concentration relative to compound of formula (III).

Fifth Aspect:
Reaction (d') of Scheme 1:

Example 120

To a solution of 1-(2,4-dichlorophenyl)cyclopropanecarbaldehyde (2.1 g, 9.3 mmol) in chlorobenzene (9 mL) was added at rt AlCl$_3$ (1.9 g, 14 mmol). The resulting yellowish suspension was heated at 60° C. for 30 min. After cooling down to 35° C., CH$_3$CN (4.38 mL, 83.7 mmol) and AcCl (1.70 mL, 23.3 mmol) were added. A slight exotherm was observed upon addition of AcCl. The reaction was heated up to 50° C. for 30 min, then, after cooling down to 5° C., the reaction mixture was added drop wise to a 0° C. cold aqueous solution of 4N NaOH (46 mL) and 50 mL of toluene. A pale yellow precipitate formed during addition. The internal temperature was maintained between 0° C. and 5° C. The bi-phasic suspension was transferred into a 250 mL separation funnel containing 200 mL of toluene. The aqueous phase was extracted twice with toluene (250 and 50 mL), the combined organic phases were washed once with a 1N aqueous NaOH solution (50 mL) and with water (2×50 mL; until pH of aqueous phase was neutral). Combined organics were then dried over solid Na$_2$SO$_4$, filtered and concentrated under reduced pressure. N-[2-(2,4-dichlorophenyl)cyclobuten-1-yl]acetamide (2.3 g) was obtained as a yellow solid.

$^1$H NMR (400 MHz, DMSO-d$_6$) δ 9.30 (bs, 1H), 7.51 (s, 1H), 7.47 (m, 2H), 2.85 (m, 2H), 2.68 (m, 2H), 1.92 (s, 3H).

Examples 121-125

The following compounds of Table 14 were prepared in an analogous manner to example 120:

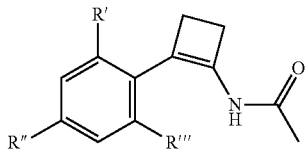

TABLE 14

| Example | R' | R" | R''' | ¹H NMR |
|---|---|---|---|---|
| 121 | F | F | F | ¹H NMR (400 MHz, CDCl₃) δ 7.51 (bs, 1H), 6.65 (m, 2H), 3.1 (bs, 2H), 2.76 (bs, 2H), 2.08 (s, 3H). |
| 122 | H | Cl | H | ¹H NMR (400 MHz, DMSO-d₆) δ 9.58 (bs, 1H), 7.36 (s, 4H), 2.88 (m, 2H), 2.46 (m, 2H), 2.02 (s, 3H). |
| 123 | Cl | H | H | ¹H NMR (400 MHz, DMSO-d₆) δ 9.76 (bs, 1H), 7.38 (m, 2H), 7.29 (t, J = 8 Hz, 1H), 7.21 (t, J = 8 Hz, 1H), 2.87 (t, J = 3.5 Hz, 2H), 2.69 (t, J = 3.5 Hz, 2H), 1.94 (s, 3H). |
| 124 | Cl | F | H | ¹H NMR (400 MHz, Acetone-d₆) δ 8.94 (bs, 1H), 7.41 (dd, J = 8.62 and 6.4 Hz, 1H), 7.22 (dd, J = 8.8 and 2.6 Hz, 1H), 7.09 (dt, J = 2.6 and 8.4 Hz, 1H), 2.99 (t, J = 3.5 Hz, 2H), 2.74 (t, J = 3.3 Hz, 2H), 2.02 (s, 3H). |
| 125 | F | F | H | ¹H NMR (400 MHz, CDCl₃) δ 7.73 (bs, 1H), 7.09 (dt, J = 6.6 and 8.4 Hz, 1H), 6.92-6.77 (m, 2H), 3.09 (t, J = 3.3 Hz, 2H), 2.56 (t, J = 3.5 Hz, 2H), 2.08 (s, 3H). |

Sixth Aspect:
Reaction (e) of Scheme 1:

Examples 126-131

Pre-Formation of Catalyst

A vial was charged with bis(COD)rhodium(I)trifluoromethanesulfonate precatalyst (0.01 mmol) and (R)-1-[(S)-2-(Di-tert-butylphosphino)ferrocenyl]ethyldi-o-tolylphosphine (0.011 mmol) in a glove box. Subsequently, the corresponding solvent (10.0 mL) was added and the solution was stirred for 90 minutes at rt.

Asymmetric Hydrogenation:

A pressure autoclave was charged with N-[2-(2,4-dichlorophenyl)cyclobuten-1-yl]acetamide (0.97 mmol), the corresponding solvent (1.50 mL) and the previously prepared catalyst solution (1.00 mL). A hydrogen pressure of 10 bar was applied and the reaction mixture was heated to 50° C. The reaction mixture was cooled to rt after a stirring period of 2 h at 50° C.

The reaction mixture was concentrated under reduced pressure and analyzed by quantitative ¹HNMR and chiral HPLC (method 4).

TABLE 15

| Example | Solvent | Conversion [%] | Selectivity [%] | ee [%] (S, S) |
|---|---|---|---|---|
| 126 | TFE | >99 | >99 | 86 |
| 127 | THF | 67 | >99 | 92 |
| 128 | DCE | 38 | >99 | 90 |
| 129 | EtOAc | 50 | >99 | 90 |
| 130 | MeTHF | 45 | >99 | 88 |
| 131 | Acetone | 50 | >99 | 86 |

TFE: 2,2,2-tetrafluroroethanol; DCE: 1 2-dichloroethane. The term "selectivity" as used in the above table refers to the selectivity of the reaction to compounds of formula (VI).

Examples 132-133

Pre-Formation of Catalyst

A vial was charged with bis(COD)rhodium(I)trifluoromethanesulfonate precatalyst (0.01 mmol) and (R)-1-[(S)-2-(Di-tert-butylphosphino)ferrocenyl]ethyldi-o-tolylphosphine (0.011 mmol) in a glove box. Subsequently, MeOH (5.00 mL) was added and the solution was stirred for 30 minutes at rt.

Asymmetric Hydrogenation:

A pressure autoclave was charged with N-[2-(2,4-dichlorophenyl)cyclobuten-1-yl]acetamide (0.98 mmol), MeOH (4.00 mL) and the previously prepared catalyst solution (1.00 mL). The corresponding hydrogen pressure was applied and the reaction mixture was heated to 50° C. The reaction mixture was cooled to rt after a stirring period of 2 h at 50° C.

The reaction mixture was concentrated under reduced pressure and analyzed by quantitative ¹HNMR and chiral HPLC (method 4).

TABLE 16

| Example | H₂ Pressure [Bar] | Conv. [%] | Selectivity [%] | ee [%] (S, S) |
|---|---|---|---|---|
| 132 | 10 | >99 | >90 | 85 |
| 133 | 50 | >99 | >90 | 88 |

The term "selectivity" as used in the above table refers to the selectivity of the reaction to compounds of formula (VI).

Examples 134-135

Pre-Formation of Catalyst

A vial was charged with bis(COD)rhodium(I)trifluoromethanesulfonate precatalyst (0.01 mmol) and (R)-1-[(S)-2-(Di-tert-butylphosphino)ferrocenyl]ethyldi-o-tolylphosphine (0.011 mmol) in a glove box. Subsequently, MeOH (5.00 mL) was added and the solution was stirred for 30 minutes at rt.

Asymmetric Hydrogenation:

A pressure autoclave was charged with N-[2-(2,4-dichlorophenyl)cyclobuten-1-yl]acetamide (0.98 mmol), MeOH (4.00 mL) and the previously prepared catalyst solution (1.00 mL). A hydrogen pressure of 50 bar was applied and the reaction mixture was heated to the temperature specified in the table. The reaction mixture was cooled to rt after a stirring period of 2 h at the temperature specified in the table. The reaction mixture was concentrated under reduced pressure and analyzed by quantitative ¹HNMR and chiral HPLC (method 4).

TABLE 17

| Example | T [° C.] | Conversion [%] | Selectivity [%] | ee [%] (S, S) |
|---------|----------|----------------|-----------------|---------------|
| 134 | rt | 98 | >90 | 88 |
| 135 | 50 | 100 | >90 | 89 |

The term "selectivity" as used in the above table refers to the selectivity of the reaction to compounds of formula (VI).

Examples 136-139

Pre-Formation of Catalyst

A vial was charged with corresponding precatalyst (0.01 mmol) and (R)-1-[(S)-2-(Di-tert-butylphosphino)ferrocenyl]ethyldi-o-tolylphosphine (0.011 mmol) in a glove box. Subsequently, the corresponding solvent (10.0 mL) was added and the solution was stirred for 90 minutes at rt.

Asymmetric Hydrogenation:

A pressure autoclave was charged with N-[2-(2,4-dichlorophenyl)cyclobuten-1-yl]acetamide (0.97 mmol), the corresponding solvent (1.50 mL) and the previously prepared catalyst solution (1.00 mL). A hydrogen pressure of 10 bar was applied and the reaction mixture was heated to 50° C. The reaction mixture was cooled to rt after a stirring period of 2 h at 50° C.

The reaction mixture was concentrated under reduced pressure and analyzed by quantitative $^1$HNMR and chiral HPLC (method 4).

TABLE 18

| Example | Rh precatalyst | Solvent | Conversion [%] | Selectivity [%] | ee [%] (S, S) |
|---------|----------------|---------|----------------|-----------------|---------------|
| 136 | [Rh(COD)$_2$]O$_3$SCF$_3$ | THF | 67 | >99 | 88 |
| 137 | [Rh(COD)$_2$]BF$_4$ | THF | 21 | >99 | 88 |
| 138 | [Rh(COD)$_2$]BARF | THF | 77 | >99 | 90 |
| 139 | [Rh(nbd)$_2$]BF$_4$ | THF | 63 | >99 | 92 |

The term "selectivity" as used in the above table refers to the selectivity of the reaction to compounds of formula (VI).

Examples 140-149

Different preformed Rh-catalysts were tested in a screening platform. The reaction vessel was charged with N-[2-(2,4-dichlorophenyl)cyclobuten-1-yl]acetamide (31.7 μmol), the corresponding catalyst (0.158 μmol) and the corresponding solvent (500 μL). A hydrogen pressure of 50 bar was applied and the reaction mixture was heated to 50° C. After a stirring period of 16 h the reaction mixture was cooled to rt and analyzed via achiral (method 3) and chiral HPLC (method 4).

TABLE 19

| Example | Catalyst | Solvent | Conversion[%] | Selectivity [%] | ee (S, S) [%] |
|---------|----------|---------|---------------|-----------------|---------------|
| 140 | [Rh(COD)((1S,1'S,2R,2'R)-2,2'-Di-tert-butyl-2,3,2',3'-tetrahydro-1H,1'H(1,1')biisophosphindolyl)]BF$_4$ | MeOH | 47.6 | 55.8 | 6.1 |
| 141 | [Rh(COD)((1S,1'S,2R,2'R)-2,2'-Di-tert-butyl-2,3,2',3'-tetrahydro-1H,1'H(1,1')biisophosphindolyl]BF$_4$ | THF | 52.6 | 41.3 | 5.5 |
| 142 | [Rh(COD)((R,R)-1,2-Bis[(2-methoxyphenyl)(phenylphosphino)]ethane)]BF$_4$ | MeOH | 93.2 | 82.1 | 0.9 |
| 143 | [Rh(COD)((R,R)-1,2-Bis[(2-methoxyphenyl)(phenylphosphino)]ethane)]BF$_4$ | THF | 99.8 | 81.9 | −14.7 |
| 144 | [Rh(COD)((S)-tert-butylmethylphosphino-di-tert-butylphosphinomethane)]BF$_4$ | MeOH | 100.0 | 90.3 | 32.7 |
| 145 | [Rh(COD)((S)-tert-butylmethylphosphino-di-tert-butylphosphinomethane)]BF$_4$ | THF | 100.0 | 90.2 | 28.4 |
| 146 | [Rh(COD)((−)-1,2-Bis[(2R,5R)-2,5-diethylphospholano]benzene)]O$_3$SCF$_3$ | MeOH | 69.7 | 49.3 | −1.3 |
| 147 | [Rh(COD)((−)-1,2-Bis[(2R,5R)-2,5-diethylphospholano]benzene)]O$_3$SCF$_3$ | THF | 60.9 | 47.0 | −7.2 |
| 148 | [Rh(COD)(3,4-bis[(2R,5R)-2,5-dimethylphospholan-1-yl]furan-2,5-dione)]O$_3$SCF$_3$ | MeOH | 70.7 | 55.2 | 0.5 |
| 149 | [Rh(COD)(3,4-bis[(2R,5R)-2,5-dimethylphospholan-1-yl]furan-2,5-dione]]O$_3$SCF$_3$ | THF | 72.2 | 57.2 | 7.0 |

The term "selectivity" as used in the above table refers to the selectivity of the reaction to compounds of formula (VI).

Examples 150-166

Pre-Formation of Catalyst

A vial was charged with [Rh(COD)$_2$]O$_3$SCF$_3$ (0.158 µmol) and the corresponding chiral ligand (0.190 µmol) in a glove box. Subsequently, dichloroethane was added and the solution was stirred for 30 minutes at rt before the solvent was evaporated under reduced pressure.

Asymmetric Hydrogenation:

N-[2-(2,4-dichlorophenyl)cyclobuten-1-yl]acetamide (31.7 µmol) and MeOH (500 µL) were added to the previously prepared catalyst. A hydrogen pressure of 50 bar was applied and the reaction mixture was heated to 50° C. The reaction mixture was cooled to rt after a stirring period of 16 h at 50° C.

The reaction mixture was concentrated under reduced pressure and analyzed via achiral (method 3) and chiral HPLC (method 4).

TABLE 20

| Example | Ligand | Yield [%] | Selectivity [%] | ee [%] |
|---|---|---|---|---|
| 150 | (R)-1-[(S)-2-(Di-tert-butylphosphino)ferrocenyl]ethyldi-o-tolylphosphine | 100.0 | 89.9 | 93.7 (S, S) |
| 151 | (S,S)$_{Fc}$-1,1'-Bis[bis(4-methoxy-3,5-dimethylphenyl)phosphino]-2,2'-bis[(R,R)$_C$-(N,N-dimethylamino)phenylmethyl]ferrocene | 100.0 | 90.2 | 22.4 (R, R) |
| 152 | (R)-1-[(S)-2-cyclohexylphosphino)ferrocenyl]ethyl bis(2-methylphenyl)-phosphine | 100.0 | 89.5 | 85.6 (S, S) |
| 153 | (R)-1-Diphenylphosphino-2-[(R)-(N,N-dimethylamino)[2-(diphenylphosphino)phenyl]methyl]ferrocene | 100.0 | 91.8 | 5.9 (R, R) |
| 154 | (R,R)-(−)-2,3-Bis(tert-butylmethylphosphino)quinoxaline | 94.5 | 73.4 | 24.1 (S, S) |
| 155 | (2R,3R)-(−)-2,3-Bis(diphenylphosphino)bicyclo[2.2.1]hept-5-ene | 99.2 | 86.2 | 9.3 (R, R) |
| 156 | (S)-2,2'-Bis(diisopropylphosphino)-6,6'-dimethoxy-1,1'-biphenyl | 100.0 | 89.3 | 26.5 (S, S) |
| 157 | (2S,4S)-(−)-2,4-Bis(diphenylphosphino)pentane | 100.0 | 91.4 | 3.0 (S, S) |
| 158 | 1,1'-Bis[(S)$_P$-[(S)$_{Fc}$-2-[(R)$_C$-1-(dimethylamino)ethyl]ferrocenyl]phenylphosphino]ferrocene | 11.3 | 19.3 | 73.0 (R, R) |
| 159 | 1-Dicyclohexylphosphino-1'-[(S)$_P$-[(S)$_{Fc}$-2-[(R)$_C$-1-(dimethylamino)ethyl]ferrocenyl]phenylphosphino]ferrocene | 97.1 | 87.6 | 68.8 (S, S) |
| 160 | (R)-1-[(S)-2-(Diphenylphosphino)ferrocenyl]ethyldi(3,5-xylyl)phosphine | 99.9 | 91.3 | 20.0 (S, S) |
| 161 | (S)$_{Fc}$-1-[(R)$_P$-tert-Butylphosphinoyl]-2-[(R)-1-(diphenylphosphino)ethyl]ferrocene | 100.0 | 90.0 | 72.1 (R, R) |
| 162 | (R)-1-[(S)-2-(Diphenylphosphino)ferrocenyl]ethyldi-tert-butylphosphine | 100.0 | 91.3 | 73.9 (R, R) |
| 163 | (R)-1-[(S)-2-(Diphenylphosphino)ferrocenyl]ethyldicyclohexylphosphine ethanol adduct | 100.0 | 89.6 | 70.3 (R, R) |
| 164 | (R)-2,2'-Bis(diphenylphosphino)-6,6'-dimethoxy-1,1'-biphenyl | 98.1 | 84.5 | 7.2 (S, S) |
| 165 | (R)-(+)-1,2-Bis(diphenylphosphino)propane | 78.3 | 38.5 | 10.9 (S, S) |
| 166 | (R)-1-[(S)-2-[Di(1-naphthyl)phosphino]ferrocenyl]ethyldi-tert-butylphosphine | 100.0 | 85.5 | 22.3 (S, S) |

The term "selectivity" as used in the above table refers to the selectivity of the reaction to compounds of formula (VI).

Examples 167-172

Pre-Formation of Catalyst

A vial was charged with [Rh(COD)$_2$]O$_3$SCF$_3$ (4.52 mg, 0.0096 mmol) and the corresponding chiral ligand (0.01208 mmol) in a glove box. Subsequently, argon degassed trifluoroethanol (10.0 mL) was added and the solution was stirred for 60 minutes at rt.

Asymmetric Hydrogenation:

A pressure autoclave was charged with N-[2-(2,4-dichlorophenyl)cyclobuten-1-yl]acetamide (250 mg, 0.966 mmol), trifluoroethanol (0.50 mL) and the previously prepared catalyst solution (2.00 mL). A hydrogen pressure of 10 bar was applied and the reaction mixture was heated to 50° C. The reaction mixture was cooled to rt after a stirring period of 2 h at 50° C.

The reaction mixture was concentrated under reduced pressure and analyzed via achiral (method 3) and chiral HPLC (method 4).

TABLE 21

| Ex. | Ligand | Conversion [%] | Selectivity [%] | ee [%] |
|---|---|---|---|---|
| 167 | (R)-1-[(S)-2-[Di(2-furyl)phosphino]ferrocenyl]ethyldi-tert-butylphosphine | >99 | >99 | 64 (R, R) |
| 168 | (R)-1-[(S)-2-(Di-tert-butylphosphino)ferrocenyl]ethyldiphenylphosphine | >99 | >99 | 86 (S, S) |
| 169 | (R)-1-[(S)-2-(Diphenylphosphino)ferrocenyl]ethyldi-tert-butylphosphine | >99 | >99 | 68 (R, R) |
| 170 | (R)-1-[(S)-2-(Dicyclohexylphosphino)ferrocenyl]ethyldicyclohexylphosphine | >99 | >99 | 0 |
| 171 | (R)-1-[(S)-2-[Bis(4-methoxy-3,5-dimethylphenyl)phosphino]ferrocenyl]ethyldicyclohexylphosphine | >99 | >99 | 44 (R, R) |
| 172 | (R)-1-[(S)-2-[Bis(4-methoxy-3,5-dimethylphenyl)phosphino]ferrocenyl]ethyldi-tert-butyl-phosphine | >99 | >99 | 58 (R, R) |

The term "selectivity" as used in the above table refers to the selectivity of the reaction to compounds of formula (VI).

Example 173

A mixture of Rh(COD)$_2$OTf (1.3 kg, 0.5 mol %) and (R)-1-[(S)-2-(di-tert-butylphosphino)ferrocenyl]ethyldi-o-tolylphosphine (2.1 kg, 0.7 mol %) in TFE (174 kg, 1.74 kmol) is stirred for 90 minutes at 50° C. before it is added to a suspension of N-[2-(2,4-dichlorophenyl)cyclobuten-1-yl]acetamide (142 kg, 0.55 kmol) in IPA (isopropyl alcohol, 866 kg, 14.4 kmol). The hydrogenation is performed at 50° C. and 10 bar hydrogen till complete conversion is achieved. The reaction solution (1176 kg; ee (S,S) 91%) is then transferred to the next step.

$^1$H NMR (400 MHz, DMSO-d$_6$) δ 8.1 (bs, 1H), 7.6 (d, J=4 Hz, 1H), 7.5 (m, 2H), 4.1 (m, 1H), 4.0 (m, 1H), 3.3 (s, 3H), 2.9 (quintet, J=8 Hz, 1H), 2.5 (m, 1H), 2.2 (m, 1H), 1.8 (m, 1H).

Reaction (e) of Scheme 1 Using Ru-Catalysts:

Examples 174-180

Pre-Formation of Catalyst:

A vial was charged with bis(2-methallyl)(COD)ruthenium precatalyst (3.72 mg) and (S,S)-(−)-2,3-bis(tert-butylmethylphosphino)quinoxaline (4.26 mg) in a glove box. Subsequently, argon degassed dichloromethane (3.0 mL) was added followed by methanesulfonic acid (1.2 mg). The solution was stirred for 30 minutes at rt.

Asymmetric Hydrogenation:

A pressure autoclave was charged with N-[2-(2,4-dichlorophenyl)cyclobuten-1-yl]acetamide (0.25 g, 0.97 mmol), the corresponding argon degassed solvent (2.0 mL) and a part of the previously prepared catalyst solution (0.5 mL). A hydrogen pressure of 50 bar was applied and the reaction mixture was heated to 50° C. The reaction mixture was cooled to rt after a stirring period of 2 h at 50° C.

The reaction mixture was concentrated under reduced pressure and analyzed by quantitative $^1$HNMR and chiral HPLC (method 4).

TABLE 22

| Example | Solvent | Conversion [%] | Selectivity [%] | ee [%] (S, S) |
|---|---|---|---|---|
| 174 | TFE | 0 | 0 | 0 |
| 175 | Acetone | 94 | 98 | 95 |
| 176 | iPrOH | 100 | 100 | 94 |
| 177 | DCE | 91 | 97 | 94 |
| 178 | THF | 50 | 98 | 96 |
| 179 | MeTHF | 75 | 95 | 96 |
| 180 | MeOH | 100 | 100 | 97 |

The term "selectivity" as used in the above table refers to the selectivity of the reaction to compounds of formula (VI).

Examples 181-182

Pre-Formation of Catalyst:

A vial was charged with bis(2-methallyl)(COD)ruthenium (6.2 mg) and (S,S)-(−)-2,3-bis(tert-butylmethylphosphino)quinoxaline (7.1 mg) in a glove box. Subsequently, argon degassed dichloromethane (4.0 mL) was added followed by fluoroboric acid-diethyl ether complex (0.24 ml, 0.081 mmol/mL). The solution was stirred for 30 minutes at rt. The volume in the vial was reduced by bubbling argon through the solution (final volume: 1 mL) before degassed MeOH (9 mL) was added.

Asymmetric Hydrogenation:

A pressure autoclave was charged with N-[2-(2,4-dichlorophenyl)cyclobuten-1-yl]acetamide (0.5 g, 1.933 mmol), argon degassed MeOH (4.0 mL) and a part of the previously prepared catalyst solution (1.0 mL). The corresponding hydrogen pressure was applied and the reaction mixture was heated to 50° C. The reaction mixture was cooled to rt after a stirring period of 2 h at 50° C.

The reaction mixture was concentrated under reduced pressure and analyzed by quantitative $^1$HNMR and chiral HPLC (method 4).

TABLE 23

| Example | H$_2$ Pressure [bar] | Conversion [%] | Selectivity [%] | ee [%] (S, S) |
|---|---|---|---|---|
| 181 | 10 | 67 | >99 | n.d. |
| 182 | 50 | >99 | >99 | 96 |

The term "selectivity" as used in the above table refers to the selectivity of the reaction to compounds of formula (VI).
n.d. = not determined.

Examples 183

Pre-Formation of Catalyst:

A vial was charged with bis(COD)tetra[u-trifluoroacetato]diruthenium(II) hydrate (1.40 mg, 0.0015 mmol), (S,S)-(−)-2,3-bis(tert-butylmethylphosphino)quinoxaline (1.10 mg, 0.0032 mmol) and N-[2-(2,4-dichlorophenyl)cyclobuten-1-yl]acetamide (0.40 g, 1.53 mmol). Subsequently, the vials were inertised with argon and argon degassed MeOH (5.0 mL) was added. A hydrogen pressure of 50 bar was applied and the reaction mixture was heated to 50° C. The reaction mixture was cooled to rt after a stirring period of 2.5 h at 50° C.

The reaction mixture was concentrated under reduced pressure and analyzed by quantitative $^1$HNMR and chiral HPLC (method 4).

TABLE 24

| Example | Rh precatalyst | Conversion [%] | Selectivity [%] | ee [%] (S, S) |
|---|---|---|---|---|
| 183 | [Ru(cod)(CF$_3$CO$_2$)$_2$]$_2$ × n H$_2$O | 84 | 95 | 94 |

The term "selectivity" as used in the above table refers to the selectivity of the reaction to compounds of formula (VI).

Examples 184-199

Pre-Formation of Catalyst

A vial was charged with the corresponding catalyst precursor (0.158 μmol; when [Ru(COD)(2-metallyl)$_2$] was applied as the catalyst precursor HBF$_4$ (0.316 μmol) was as well charged to the vial)) and the corresponding chiral ligand (0.19 μmol) in a glove box. Subsequently, dichloroethane was added and the solution was stirred for 30 minutes at rt before the solvent was evaporated under reduced pressure.

Asymmetric Hydrogenation:

N-[2-(2,4-dichlorophenyl)cyclobuten-1-yl]acetamide (31.7 μmol) and MeOH (500 μL) were added to the previously prepared catalyst. A hydrogen pressure of 50 bar was applied and the reaction mixture was heated to 50° C. The reaction mixture was cooled to rt after a stirring period of 16 h at 50° C. The reaction mixture was concentrated under reduced pressure and analyzed via achiral (method 3) and chiral HPLC (method 4).

TABLE 25

| Ex. | Catalyst Precursor | Ligand | Remark | Conv. [%] | Select. [%] | ee [%] |
|---|---|---|---|---|---|---|
| 184 | [RuCl$_2$(p-cymene)]$_2$ | (R)-(+)-2,2'-Bis[di(3,5-xylyl)phosphino]-1,1'-binaphthyl | | 100.0 | 48.6 | 80.2 (R, R) |
| 185 | [Ru(COD)(2-metallyl)$_2$] | (R)-(+)-2,2'-Bis[di(3,5-xylyl)phosphino]-1,1'-binaphthyl | HBF$_4$ komplex | 100.0 | 54.8 | 85.2 (R, R) |
| 186 | [RuCl$_2$(p-cymene)]$_2$ | (S)-2,2'-Bis[di-3,5-xylylphosphino]-6,6'-dimethoxy-1,1'-biphenyl | | 98.8 | 86.4 | 60.8 (S, S) |
| 187 | [Ru(COD)(OOCCF$_3$)$_2$] | (S)-2,2'-Bis[di-3,5-xylylphosphino]-6,6'-dimethoxy-1,1'-biphenyl | | 99.2 | 81.0 | 59.0 (S, S) |
| 188 | [Ru(COD)(2-metallyl)$_2$] | (−)-1,2-Bis((2R,5R)-2,5-diethylphospholano)benzene | HBF$_4$ komplex | 100.0 | 91.4 | 81.8 (R, R) |
| 189 | [Ru(COD)(OOCCF$_3$)$_2$] | (S,S)$_{Fc}$-1,1'-Bis[bis(4-methoxy-3,5-dimethylphenyl)phosphino]-2,2'-bis[(R,R)$_C$-(N,N-dimethylamino)phenylmethyl]ferrocene | | 100.0 | 75.6 | 34.1 (S, S) |
| 190 | [Ru(COD)(2-metallyl)$_2$] | (R)-1-Diphenylphosphino-2-[(R)-(N,N-dimethylamino)[2-(diphenylphosphino)phenyl]methyl]ferrocene | HBF$_4$ komplex | 75.1 | 72.1 | 20.1 (S, S) |
| 191 | [RuCl$_2$(p-cymene)]$_2$ | (S)-2,2'-Bis[bis(3,5-di-tert-butyl-4-methoxyphenyl)phosphino]-6,6'-dimethoxy-1,1'-biphenyl | | 95.7 | 60.7 | 28.8 (R, R) |
| 192 | [Ru(COD)(OOCCF$_3$)$_2$] | (S)-2,2'-Bis[bis(3,5-di-tert-butyl-4-methoxyphenyl)phosphino]-6,6'-dimethoxy-1,1'-biphenyl | | 100.0 | 70.8 | 25.8 (R, R) |
| 193 | [Ru(COD)(2-metallyl)$_2$] | 1-Dicyclohexylphosphino-1'-[(S)$_P$-[(S)$_{Fc}$-2-[(R)$_C$-1-(dimethylamino)ethyl]ferrocenyl]phenylphosphino]ferrocene | HBF$_4$ komplex | 99.9 | 61.4 | 26.1 (S, S) |
| 194 | [Ru(COD)(OOCCF$_3$)$_2$] | (R)-1-[(S)-2-(Diphenylphosphino)ferrocenyl]ethyldi(3,5-xylyl)phosphine | | 100.0 | 90.1 | 54.9 (R, R) |
| 195 | [Ru(COD)(2-metallyl)$_2$] | (R,R)-(−)-2,3-Bis(tert-butylmethylphosphino)quinoxaline | HBF$_4$ komplex | 99.9 | 90.4 | 96.2 (R, R) |
| 196 | [Ru(COD)(OOCCF$_3$)$_2$] | (R)-1-[(S)-2-(Diphenylphosphino)ferrocenyl]ethyldi-tert-butylphosphine | | 100.0 | 83.2 | 69.7 (R, R) |
| 197 | [Ru(COD)(2-metallyl)$_2$] | (2R,3R)-(+)-2,3-Bis(diphenylphosphino)butane | HBF$_4$ komplex | 100.0 | 85.3 | 24.8 (R, R) |

TABLE 25-continued

| Ex. | Catalyst Precursor | Ligand | Remark | Conv. [%] | Select. [%] | ee [%] |
|---|---|---|---|---|---|---|
| 198 | [Ru(COD)(OOCCF$_3$)$_2$] | (R)-2,2'-Bis(diphenylphosphino)-6,6'-dimethoxy-1,1'-biphenyl | | 99.2 | 82.6 | 65.7 (R, R) |
| 199 | [Ru(COD)(2-metallyl)$_2$] | (R)-(+)-1,2-Bis(diphenylphosphino)propane | HBF$_4$ komplex | 100.0 | 88.8 | 3.3 (R, R) |

The term "selectivity" as used in the above table refers to the selectivity of the reaction to compounds of formula (VI).

Examples 200-206

Pre-Formation of Catalyst

A vial was charged with bis(2-methallyl)(COD)ruthenium (3.10 mg, 0.0097 mmol), the corresponding chiral ligand (0.0107 mmol) and fluoroboric acid diethylether complex (1.72 mg, 0.0106 mmol) in a glove box. Subsequently, argon degassed dichloromethane (2.5 mL) was added and the solution was stirred for 30 minutes at rt.

Asymmetric Hydrogenation:

A pressure autoclave was charged with N-[2-(2,4-dichlorophenyl)cyclobuten-1-yl]acetamide (250 mg, 0.97 mmol), argon degassed MeOH (2.0 mL) and the previously prepared catalyst solution (0.5 mL). A hydrogen pressure of 50 bar was applied and the reaction mixture was heated to 50° C. The reaction mixture was cooled to rt after a stirring period of 2 h at 50° C.

The reaction mixture was concentrated under reduced pressure and analyzed analyzed via achiral (method 3) and chiral HPLC (method 4).

TABLE 26

| Example | Ligand | Conv. [%] | Select. [%] | ee [%] |
|---|---|---|---|---|
| 200 | (S)-1-[(R)-2-(Diphenylphosphino)ferrocenyl]ethyldi-tert-butylphosphine | 90 | 95 | 72 (S, S) |
| 201 | (S)-1-[(R)-2-[Di(2-furyl)phosphino]ferrocenyl]ethyldi-tert-butylphosphine | >99 | >99 | 56 (S, S) |
| 202 | (R,R)-(+)-1,2-Bis(t-butylMethylphosphino)benzene | 98 | >99 | 94 (R, R) |
| 203 | (−)-1,2-Bis[(2R,5R)-2,5-dimethylphospholano]benzene | 91 | 95 | 80 (R, R) |
| 204 | (+)-1,2-Bis[(2S,5S)-2,5-diethylphospholano]benzene | >99 | 98 | 79 (S, S) |
| 205 | (−)-1,2-Bis((2S,5S)-2,5-diethylphospholano)ethane | 83 | 87 | 76 (R, R) |
| 206 | (1S,1S',2R,2R')-1,1'-Di-tert-butyl-(2,2')-diphospholane | 56 | 92 | 79 (R, R) |

The term "selectivity" as used in the above table refers to the selectivity of the reaction to compounds of formula (VI).

Examples 207-208

Pre-Formation of Catalyst

A vial was charged with bis(2-methallyl)(COD)ruthenium (3.72 mg, 0.0116 mmol) and the corresponding chiral ligand (0.0127 mmol) in a glove box. Subsequently, argon degassed dichloromethane (3.00 mL) and a 0.081M solution of methane sulfonic acid in dichloromethane (0.16 mL, 0.0130 mmol) was added and the solution was stirred for 30 minutes at rt.

Asymmetric Hydrogenation:

A pressure autoclave was charged with N-[2-(2,4-dichlorophenyl)cyclobuten-1-yl]acetamide (250 mg, 0.97 mmol), argon degassed MeOH (2.0 mL) and the previously prepared catalyst solution (0.5 mL). A hydrogen pressure of 50 bar was applied and the reaction mixture was heated to 50° C. The reaction mixture was cooled to rt after a stirring period of 2 h at 50° C.

The reaction mixture was concentrated under reduced pressure and analyzed via achiral and chiral HPLC.

TABLE 27

| Example | Ligand | Conv. [%] | Select. [%] | ee [%] |
|---|---|---|---|---|
| 207 | (S)-1-[(R)-2-[Bis(4-methoxy-3,5-dimethylphenyl)phosphino]ferrocenyl]ethyldi-tert-butyl-phosphine | >99 | 95 | 85 (S, S) |
| 208 | (S)-1-[(R)-2-[Bis(4-methoxy-3,5-dimethylphenyl)phosphino]ferrocenyl]ethyldicyclohexylphosphine | 95 | 98 | 86 (S, S) |

The term "selectivity" as used in the above table refers to the selectivity of the reaction to compounds of formula (VI).

Seventh Aspect:
Reaction (f) of Scheme 1:

Example 209

A reaction mixture consisting of N-[(1S,2S)-2-(2,4-dichlorophenyl)cyclobutyl]acetamide in isopropanol/trifluoroethanol (428 g, 153 mmol) and a suspension of aerosil-200 (23 mg) in isopropanol (0.5 g) was heated to Ta=130° C. A part of the isopropanol and the trifluoroethanol (ca. 220 g) was removed at a temperature of 82° C. measured at the head of the distillation equipment before a 50% aqueous $H_3PO_4$ solution (150 g, 765 mmol) was added. More isopropanol and trifluoroethanol was removed till the temperature at the top of the distillation column reached 100° C. Subsequently, the reaction mass was stirred under reflux conditions till a conversion >95% was achieved (reaction time: about 20 h). Water (145 g, 8.1 mol) was added to the reaction mixture once it was cooled to Ti=60° C. The reaction mixture was extracted twice with toluene (first: 169 g, 1.8 mol; second: 86 g, 0.9 mol) before the pH of the aqueous solution was adjusted to 8.0-8.5 using a 25% aqueous ammonia solution (117.5 g, 1.7 mol). The basic aqueous phase was extracted with toluene (169 g, 1.8 mol). Subsequently, the organic layer was concentrated under reduced pressure and filtered to obtain a 25.3% solution of (1S,2S)-2-(2,4-dichlorophenyl)cyclobutanamine in toluene (136 g).

$^1$H NMR (400 MHz, CDCl$_3$) δ 7.54 (t, J=4 Hz, 1H), 7.41 (d, J=4 Hz, 2H); 3.86-3.75 (m, 2H), 2.41-2.24 (m, 2H), 2.13-2.00 (m, 1H), 1.60-1.53 (m, 1H).

Example 210

A reaction mixture consisting of N-[(1S,2S)-2-(2,4-dichlorophenyl)cyclobutyl]acetamide (10 g, 35.8 mmol), methane sulfonic acid (6.9 g, 71.5 mmol) and water (6.4 g, 358 mmol) was heated to 110° C. to achieve reflux conditions. The reaction mass was stirred under reflux conditions for 21 h before it was cooled to rt. Water (40 mL) was added to the reaction mixture and subsequently extracted twice with toluene (first: 50 mL; second: 30 mL). The pH of the aqueous solution was adjusted to 8.9 using a 25% aqueous ammonia solution (9.6 g, 141 mmol). The basic aqueous phase was extracted with toluene (50 mL) to obtain a 11.9% solution of (1S,2S)-2-(2,4-dichlorophenyl)cyclobutanamine in toluene (59.8 g).

Example 211

N-[(1S,2S)-2-(2,4-dichlorophenyl)cyclobutyl]acetamide (5.0 g, 17.9 mmol) was added to a 60% aqueous $H_2SO_4$ solution (17.5 g, 107 mmol). The reaction mixture was heated to 128° C. to achieve reflux conditions. The reaction mass was cooled to 60° C. after a stirring period of 21 h at reflux conditions. Water (75 mL) was added to the reaction mixture and subsequently extracted twice with toluene (first: 25 mL; second: 25 mL). The pH of the aqueous solution was adjusted to 8.8 using a 25% aqueous ammonia solution (5.8 g, 85.1 mmol). The basic aqueous phase was extracted with toluene (100 mL). Subsequently, the organic layer was concentrated under reduced pressure to obtain a 15.4% solution of (1S,2S)-2-(2,4-dichlorophenyl)cyclobutanamine in toluene (17.3 g).

Eighth Aspect:
Reaction (g) of Scheme 1:

Example 212

A solution of (1S,2S)-2-(2,4-dichlorophenyl)cyclobutanamine in toluene (339 g, 0.40 mol) is added to solid NaHCO$_3$(47 g, 0.56 mol). Water (140 g, 7.79 mol) is then added to the reaction mixture and the mixture is heated to Ti=50° C. Subsequently, a solution of 2-(trifluoromethyl)pyridine-3-carbonyl chloride in toluene (247 g, 0.42 mol) is added over 53 minutes at Ti=50° C. to the reaction mixture. Once complete conversion is achieved the reaction mixture is heated to Ti=70° C. and stirred for 20 minutes at this temperature. After phase separation the organic phase is extracted with water (201 g, 11.1 mol) at Ti=80° C. Subsequent to the phase separation the organic phase is concentrated to a ca. 35% solution MCH (140 g, 1.4 mol) is then added over 20 minutes to the concentrated organic phase at Ti=80° C. The reaction mixture is then cooled down to Ti=5° C. over 2.5 h whereas seeds are added at Ti=72° C. (crystallization works also without seeding). The reaction mixture is stirred for 30 minutes once the reaction mixture reached a Ti of 5° C. before the suspension is filtered, washed with MCH (200 g, 2.0 mol) and dried at elevated temperature under reduced pressure to isolate N-[(1S,2S)-2-(2,4-dichlorophenyl)cyclobutyl]-2-(trifluoromethyl) pyridine-3-carboxamide (141.6 g) as an anhydrate. FT-1R 3282, 3077, 2981, 2952, 1650, 1593, 1543, 1473, 1353, 1187, 1138, 1074, 1066, 1054 cm' The anhydrate of N-[(1S,2S)-2-(2,4-dichlorophenyl)cyclobutyl]-2-(trifluoromethyl) pyridine-3-carboxamide (80 g) was dissolved in a mixture of acetone (240 g, 4.1 mol) and water (80 g, 4.4 mol) at Ti=55° C. The mixture was then cooled to Ti=8° C. and seed crystals were added at Ti=29° C. Water (86 g, 4.8 mol) was added over 60 minutes to the reaction mixture once the reaction mixture reached a temperature of 8° C. The reaction mixture was stirred for 30 minutes after adding another aliquot of water (174 g, 9.7 mol) over 1 h. Subsequently, the final aliquot of water (340 g, 18.9 mol) was added and the suspension was stirred for 80 minutes. The suspension was filtered and the filter cake was washed with water (2×80 g, 4.) before it was dried under reduced pressure at 35° C. to yield the monohydrate of N-[(1S,2S)-2-(2,4-dichlorophenyl)cyclobutyl]-2-(trifluoromethyl) pyridine-3-carboxamide (94.6 g).

$^1$H NMR (400 MHz, CDCl$_3$) δ 8.65 (dd, J=4.6 Hz, J=1.2 Hz, 1H), 7.60-7.58 (m, 1H), 7.47-7.44 (m, 1H), 7.41-7.40 (m, 1H), 7.33-7.25 (m, 2H), 5.54 (br d, J=7.8 Hz, 1H), 5.03

(quin, J=7.3 Hz, 1H), 4.24 (q, J=7.8 Hz, 1H), 2.65-2.56 (m, 1H), 2.44-2.28 (m, 2H), 2.10-2.01 (m, 1H).

FT-1R 3403, 3232, 3079, 2948, 1660, 1645, 1593, 1575, 1471, 1326, 1186, 1126, 1076, 1054 cm'.

Example 213

A biphasic mixture of (1S,2S)-2-(2,4-dichlorophenyl)cyclobutanamine (20.0 g, 87.3 mmol) in toluene (20 g) and water (40 g) was cooled to 0° C. and seed crystals of the product in hydrate form (1.53 g) were added. A solution of 2-(trifluoromethyl)pyridine-3-carbonyl chloride (19.7 g, 91.6 mmol) in toluene (60 g) is dosed in parallel to 30% aq NaOH (14.0 g, 105 mmol) over 2 h in such a way that pH is kept between 7-9. After the end of dosing the reaction was stirred for further 3 h. The resulting thick suspension was filtered, the filter cake was washed with water (2×25 g) and dried at 150 mbar pressure for 16 h to yield N-[(1S,2S)-2-(2,4-dichlorophenyl)cyclobutyl]-2-(trifluoromethyl) pyridine-3-carboxamide (36.4 g, containing 7% water) as a monohydrate.

FT-IR 3403, 3232, 3079, 2948, 1660, 1645, 1593, 1575, 1471, 1326, 1186, 1126, 1076, 1054 cm'.

What is claimed is:

1. A process for the preparation of enantiomerically and diastereomerically enriched cyclobutane amides comprising
    (a) reducing the nitrile moiety of a compound of formula (I) to an aldehyde

wherein A is selected from aryl, heteroaryl, $C_1$-$C_6$-alkyl, $C_2$-$C_6$-alkenyl, $C_2$-$C_6$-alkynyl and $C_3$-$C_7$-cycloalkyl, which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl;
    wherein the reduction of the nitrile moiety of the compound of formula (I) is carried out via partial hydrogenation to the corresponding intermediate imine applying $H_2$ and a metal hydrogenation catalyst, followed by subsequent hydrolysis to the compound of formula (II)

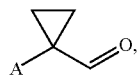

then
    (b) reacting the compound of formula (II) in the presence of a suitable Lewis acid to obtain a compound of formula (III)

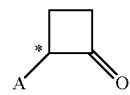

wherein * indicates a stereocentre, then
    (c) reacting a compound of formula (III) with an ammonium salt and $H_2$ in presence of a chiral transition metal catalyst to obtain an enantiomerically and diastereomerically enriched amine of formula (IV)

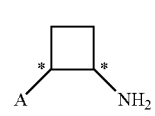

wherein * indicates a stereocentre, and then
    further reacting the amine of formula (IV) with a compound of formula (X)

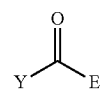

wherein Y is a suitable leaving group selected from OH, OR or halogen, R is $C_1$-$C_6$-alkyl, and E is selected from aryl, heteroaryl, hydrogen, $C_1$-$C_6$-alkyl, $C_2$-$C_6$-alkenyl, $C_2$-$C_6$-alkynyl and $C_3$-$C_7$-cycloalkyl which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl;
    so as to form the enantiomerically and diastereomerically enriched amide of formula (VII)

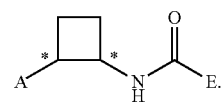

2. The process according to claim 1, wherein
    A and E are selected from aryl and heteroaryl, which aryl and heteroaryl are unsubstituted or substituted with one or more substituents independently selected from halogen, cyano, $C_1$-$C_6$-alkyl, $C_1$-$C_6$-haloalkyl, $C_1$-$C_6$-alkoxy and $C_1$-$C_6$-haloalkoxy.

3. The process according to claim 1, wherein
    A is phenyl and E is heteroaryl, which phenyl and heteroaryl are unsubstituted or substituted with one or more substituents independently selected from halogen, cyano, $C_1$-$C_6$-alkyl, $C_1$-$C_6$-haloalkyl, $C_1$-$C_6$-alkoxy and $C_1$-$C_6$-haloalkoxy.

4. The process according to claim 1, wherein the compound of formula (II) is reacted in step (b) in the presence of a Lewis acid selected from $AlCl_3$ and $GaCl_3$.

5. The process according to claim 4, wherein 1.0-1.5 mole equivalents of AlCl₃ or GaCl₃ relative to the compound of formula (II) are added in step (b).

6. The process according to claim 1, wherein the chiral transition metal catalyst in step (c) comprises a transition metal selected from Ru, Rh, Ir and Pd, and a chiral ligand with a bidentate phosphor of the general formula (VIII)

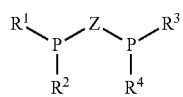

(VIII)

wherein Z is a linking group and R¹, R², R³ and R⁴ are independently selected from aryl, heteroaryl, C1-C6-alkyl and $C_3$-$C_6$-cycloalkyl, each of which is unsubstituted or substituted with one or more substituents independently selected from $C_1$-$C_6$ alkyl, $C_1$-$C_6$ alkoxy, $C_1$-$C_6$ haloalkyl and halogen.

7. The process according to claim 6, wherein the linking group Z is selected from (R and S)-1,1'-binaphthyl, (R and S)-4,4'-bi-1, 3-benzodioxole, (R and S)-2, 2', 6,6'-tetramethoxy-3, 3'-bipyridine, (R and S)-6,6'-dimethoxy-1, 1'-biphenyl, (R and S)-4,4', 6,6' tetramethoxy-1, 1'-biphenyl, 2, 2'-bis-[(R)-cx-(dimethylamino)benzyl]ferrocene, ferrocenyl methyl, ferrocene, benzene and ethyl.

8. The process according to claim 6, wherein the chiral ligand is selected from
(R)-2,2'-bis(diphenylphosphino)-1,1'-binaphthyl,
(R)-2,2'-bis(di-p-tolylphosphino)-1,1'-binaphthyl,
(R)-2,2'-bis[di(3,5-xylyl)phosphino]-1,1'-binaphthyl,
(R)-5,5'-bis(diphenylphosphino)-4,4'-bi-1,3-benzodioxole,
(R)-5,5'-bis(di[3,5-xylyl]phosphino)-4,4'-bi-1,3-benzodioxole,
(R)-5,5'-bis[di(3,5-di-tert-butyl-4-methoxyphenyl)phosphino]-4,4'-bi-1,3-benzodioxole,
(S)-1,13-bis(diphenylphosphino)-7,8-dihydro-6H-dibenzo[f,h][1,5]dioxin,
(R)-2,2',6,6'-tetramethoxy-4,4'-bis(di(3,5-xylyl)phosphino)-3,3'-bipyridine,
(R)-2,2'-bis(diphenylphosphino)-6,6'-dimethoxy-1,1'-biphenyl,
(R)-2,2'-bis(diphenylphosphino)-4,4',6,6'-tetramethoxy-1,1'-biphenyl,
(R)-6,6'-bis(diphenylphosphino)-2,2',3,3'-tetrahydro-5,5'-bi-1,4-benzodioxin,
(R)-(+)-2,2'-bis(diphenylphosphino)-5,5',6,6',7,7',8,8'-octahydro-1,1'-binaphthyl,
(R)-(+)-2,2'-bis(di-3,5-xylylphosphino)-5,5',6,6',7,7',8,8'-octahydro-1,1'-binaphthyl,
(R)-5,5'-bis(diphenylphosphino)-2,2,2',2'-tetrafluoro-4,4'-bi-1,3-benzodioxole,
(S)-1-[(S)-1-[di(3,5-xylyl)phosphino]ethyl]-2-[2-[di(3,5-xylyl)phosphino]phenyl]ferrocene, and
(S)-1-[(S)-1-[bis[3,5-bis(trifluoromethyl)phenyl]phosphino]ethyl]-2-[2-(diphenylphosphino)phenyl]ferrocene.

9. The process according to claim 6, wherein the chiral transition metal catalyst is selected from [RuCl(p-cymene)((S)-DM-SEGPHOS)]Cl, [RuCl(p-cymene)((R)-DM-SEGPHOS)]Cl, [NH₂Me₂][(RuCl((R)-xylbinap))₂(u-Cl)₃], [NH₂Me₂][(RuCl((S)-xylbinap))₂(u-Cl)₃], Ru(OAc)₂[(R)-binap], Ru(OAc)₂[(S)-binap], Ru(OAc)₂[(R)-xylbinap], Ru(OAc)₂[(S)-xylbinap], RuCl₂[(R)-xylbinap][(R)-daipen], RuCl₂[(S)-xylbinap][(S)-daipen], RuCl₂[(R)-xylbinap][(R,R)-dpen] and RuCl₂[(S)-xylbinap][(S,S)-dpen].

10. A process for the preparation of a compound of formula (III)

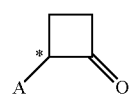

(III)

wherein A is as defined in claim 1 and * indicates a stereocentre, comprising reacting a compound of formula (II)

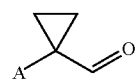

(II)

with a suitable Lewis acid.

11. A process for the preparation of a compound of formula (III)

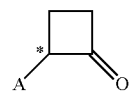

(III)

wherein A is as defined in claim 1 and * indicates a stereocentre, comprising reacting a compound of formula (II)

(II)

with a Lewis acid selected from AlCl₃ and GaCl₃.

12. The process according to claim 11, wherein 1.0-1.5 mole equivalents of AlCl₃ or GaCl₃ relative to the compound of formula (II) is added.

13. The process according to claim 10, wherein the compound of formula (III)

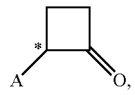

(III)

wherein A is selected from aryl, heteroaryl, $C_1$-$C_6$-alkyl, $C_2$-$C_6$-alkenyl, $C_2$-$C_6$-alkynyl and $C_3$-$C_7$-cycloalkyl, which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$- haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl and * indicates a stereocentre, is further reacted with an ammonium salt and $H_2$ in presence of a chiral transition metal catalyst to obtain an enantiomerically and diastereomerically enriched amine of formula (IV)

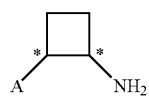

(IV)

wherein * indicates a stereocentre, and then
further reacting the amine of formula (IV) with a compound of formula (X)

(X)

wherein Y is a suitable leaving group selected from OH, OR or halogen, R is $C_1$-$C_6$-alkyl, and E is selected from aryl, heteroaryl, hydrogen, $C_1$-$C_6$-alkyl, $C_2$-$C_6$-alkenyl, $C_2$-$C_6$-alkynyl and $C_3$-$C_7$-cycloalkyl which aryl, heteroaryl, $C_1$-$C_6$-alkyl, $C_2$-$C_6$-alkenyl, $C_2$-$C_6$-alkynyl and $C_3$-$C_7$-cycloalkyl are unsubstituted or substituted with one or more substituents independently selected from halogen, cyano, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_1$-$C_6$-alkylsulfanyl, $C_1$-$C_6$-haloalkylsulfanyl, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_2$-$C_6$-haloalkenyl and $C_2$-$C_6$-haloalkynyl;

so as to form the enantiomerically and diastereomerically enriched amide of formula (VII)

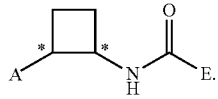

(VII)

14. The process according to claim 13, wherein the chiral transition metal catalyst comprises a transition metal selected from Ru, Rh, Ir and Pd, and a chiral ligand with a bidentate phosphor of the general formula (VIII)

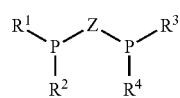

(VIII)

wherein Z is a linking group and $R^1$, $R^2$, $R^3$ and $R^4$ are independently selected from aryl, heteroaryl, $C_1$-$C_6$-alkyl and $C_3$-$C_6$-cycloalkyl, each of which is unsubstituted or substituted with one or more substituents independently selected from $C_1$-$C_6$ alkyl, $C_1$-$C_6$ alkoxy, $C_1$-$C_6$ haloalkyl and halogen.

15. A process for the preparation of a compound of formula (V)

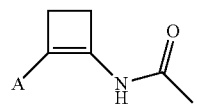

(V)

wherein A is as defined in claim 1, which comprises reacting a compound of formula (II)

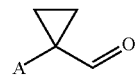

(II)

in the presence of a Lewis acid selected from $AlCl_3$ and $GaCl_3$ to obtain a compound of formula (III)

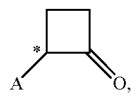

(III)

and further reacting the compound of formula (III) with acetonitrile and a suitable additive, wherein the additive is selected from acyl chlorides, anhydrides or esters.

16. The process according to claim 1, wherein Y is chloro.

17. The process according to claim 4, wherein the Lewis acid is $AlCl_3$.

18. The process according to claim 6, wherein the transition metal is Ru.

19. The process according to claim 7, wherein the linking group Z is (R and S)-1,1'-binaphthyl.

20. The process according to claim 11, wherein the Lewis acid is $AlCl_3$.

21. The process according to claim 13, wherein Y is chloro.

22. The process according to claim 15, wherein the Lewis acid is $AlCl_3$.

23. The process according to claim 15, wherein the additive is selected from acetyl chloride, isopropenyl acetate, 4-methoxybenzoyl chloride and p-anisic anhydride.

* * * * *